(12) United States Patent
McBride et al.

(10) Patent No.: US 7,045,503 B1
(45) Date of Patent: May 16, 2006

US007045503B1

(54) RADIOMETAL-BINDING PEPTIDE ANALOGUES

(75) Inventors: William J. McBride, Summit, NJ (US); Gary L. Griffiths, Morristown, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 923 days.

(21) Appl. No.: 09/676,783

(22) Filed: Oct. 2, 2000

Related U.S. Application Data

(62) Division of application No. 08/893,749, filed on Jul. 11, 1997, now Pat. No. 6,126,916.

(60) Provisional application No. 60/021,662, filed on Jul. 12, 1996.

(51) Int. Cl.
*A61K 38/16* (2006.01)

(52) U.S. Cl. .......................... 514/6; 530/300; 530/317; 530/324; 530/333; 530/334; 530/335; 530/336; 424/1.69; 424/1.11; 424/1.57; 424/1.65; 424/9.1; 514/2

(58) Field of Classification Search .................... 514/2; 630/300, 317, 324, 333, 334, 335, 336; 424/1.69, 424/1.11, 1.57, 1.65, 9.1
See application file for complete search history.

(56) References Cited

U.S. PATENT DOCUMENTS

| | | | |
|---|---|---|---|
| 4,564,472 A | 1/1986 | Ueda et al. | 260/113 |
| 4,822,890 A | 4/1989 | Bolin | 548/344 |
| 5,080,884 A | 1/1992 | McBride et al. | 424/1.1 |
| 5,225,180 A | 7/1993 | Dean et al. | 424/1.1 |
| 5,227,474 A | 7/1993 | Johnson et al. | 534/558 |
| 5,449,761 A | 9/1995 | Belinka, Jr. et al. | 534/10 |
| 5,539,138 A * | 7/1996 | Flanagan et al. | 558/17 |
| 5,556,939 A * | 9/1996 | Flanagan et al. | 530/311 |
| 5,746,996 A * | 5/1998 | Govindan et al. | 424/1.69 |
| 5,753,206 A | 5/1998 | McBride et al. | 424/1.69 |
| 5,772,981 A * | 6/1998 | Govindan et al. | 424/1.49 |

FOREIGN PATENT DOCUMENTS

| | | |
|---|---|---|
| EP | 0 536 741 | 4/1993 |
| WO | 91/01144 | 2/1991 |
| WO | 93/21962 | 11/1993 |
| WO | 93/25244 | 12/1993 |
| WO | 94/23758 | 10/1994 |
| WO | 94/26294 | 11/1994 |
| WO | 94/28942 | 12/1994 |
| WO | 96/40756 | 12/1996 |

OTHER PUBLICATIONS

Virgolini et al., "Vasoactive Intestinal Peptide-Receptor Imaging for the Localization of Intestinal Adenocarcinomas and Endocrine Tumors" *The New England Journal of Medicine* pp. 1116-1121 (1994).

Virgolini et al., "Vasoactive Intestinal Peptide Receptor Scintigraphy" *The Journal of Nuclear Medicine* 36:1732-1739 (1995).

Lister-James et al., "Radiopharmaceutical Chemistry: Protein, Peptides, Antibodies I" No. 370 36:91P, (1995).

Pearson et al., "Somatostatin Receptor-Binding Peptides Labeled with Technetium-99m: Chemistry and Initial Biological Studies" *J. Med. Chem.* 39:1361-1371 (1996).

Krenning et al., "Somatostatin Receptor Scintigraphy with Indium-111-DTPA-D-Phe-1-Octreotide in Man: Metabolism, Dosimetry and Comparison with Iodine-123-TYr-3-Octreotide" *The Journal of Nuclear Medicin* 33:652-658 (1992).

Wraight et al., "The use of a chelating derivative of alpha melanocyte stimulating hormone for the clinical imaging of melanoma" *The British Journal of Radiology* 65:112-118 (1992).

Reubi, "In Vitro Identification of Vasoactive Intestinal Peptide Receptors in Human Tumors: Implications for Tumor Imaging" *The Journal of Nuclear Medicine* 36:1846-1853 (1995).

Maina et al., "Synthesis, Radiochemical and Biological Evaluation of $^{99m}$ Tc[N4(D)Phe$^1$]-Octreotide, a New Octreotide Derivative with High Affinity for Somatostatin Receptor" *The Journal of Nuclear Biology and) Medicine* pp. 452 (1994.

Bajusz et al., "Highly potent metallopeptide analogues of luteinizing hormone-releasing hormone" *Proc. Natl. Acad. Sci. USA* 86:6313-6317 (1989).

Felix et al., "Synthesis, biological activity and conformational analysis of cyclic GRF analogs" *J. Peptide Protein Res.* 32:441-454 (1988).

Edwards et al., "Generally Applicable, Convenient Solid-Phase Synthesis and Receptor Affinities of Octreotide Analogs" *J. Med. Chem.* 37:3749-3757 (1994).

Beinstock et al., "Conformational Analysis of a Highly Potent Dicyclic Gonadotropin-Releasing Hormone Antagonist by Nuclear Magnetic Resonance and Molecular Dynamics" *American Chemical Society* pp. 3265-3273 (1993).

(Continued)

Primary Examiner—T. D. Wessendorf
(74) Attorney, Agent, or Firm—Heller Ehrman LLP

(57) ABSTRACT

Novel metal binding ligands are disclosed that may be coupled to peptides for use in methods of diagnosis and therapy. Peptides containing the ligands are produced using a method wherein ligand introduction or cyclization can be conducted at any point during the synthesis of the peptide. Such peptide derivatives are readily labeled with radiometals, such as isotopes of rhenium or technetium, while retaining their ability to tightly bind specific peptide receptors.

20 Claims, No Drawings

OTHER PUBLICATIONS

Barbacci et al., "The Structural Basis for the Specificity of Epidermal Growth Factor and Heregulin Binding" The Journal of Biological Chemistry 270:9585-9589 (1995).

Haskell-Luevano et al., "Characterizations of the Unusual Dissociation Properties of Melanotropin Peptides from the Melanocortin Receptor, hMC1R" *J. Med. Chem.* 39:432-435 (1996).

Al-Obeidi et al., "Design of a New Class of Superpotent Cyclic α-Melanotropins Based on Quenched Dynamic Simulations" *J. AM. Chem. Soc.* 111:3413-3416 (1989).

O'Donnell et al., "Ro 25-1553: A Novel, Long-Acting Vasoactive Intestinal Peptide Agonist. Part I: In Vitro and In Vivo Bronchodilator Studies" The Journal of Pharmacology and Experimental Therapeutics 270:1282-1294 (1994).

Virgolini et al., "Cross-Competition between Vasoactive Intestinal Peptide and Somatostatin for Binding to Tumor Cell Membrane Receptors[1]" *Cancer Research* pp. 690-700 (1994).

* cited by examiner

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
       (A) LENGTH: 7 amino acids
       (B) TYPE: amino acid
       (C) STRANDEDNESS: <Unknown>
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /product= "Nle"

(ix) FEATURE:
       (A) NAME/KEY: Modified-site
       (B) LOCATION: 4
       (D) OTHER INFORMATION: /note= "Xaa is D-Phe"

(xi) SEQUENCE DESCRIPTION: SEQ ID NO: 1:

Xaa Asp His Xaa Arg Trp Lys
1               5

(2) INFORMATION FOR SEQ ID NO: 2:

(i) SEQUENCE CHARACTERISTICS:
       (A) LENGTH: 28 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 2:

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
                20                  25

(2) INFORMATION FOR SEQ ID NO: 3:

(i) SEQUENCE CHARACTERISTICS:
       (A) LENGTH: 28 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 3:

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn
                20                  25

(2) INFORMATION FOR SEQ ID NO: 4:

(i) SEQUENCE CHARACTERISTICS:
       (A) LENGTH: 24 amino acids
       (B) TYPE: amino acid
       (C) STRANDEDNESS: <Unknown>
       (D) TOPOLOGY: linear (ii) MOLECULE TYPE: peptide (xi) SEQUENCE DESCRIPTION: SEQ ID NO: 4:

Val Phe Thr Asp Asn Tyr Thr Arg Leu Arg Lys Gln Met Ala Val Lys
1               5                   10                  15

Lys Tyr Leu Asn Ser Ile Leu Asn
            20

(2) INFORMATION FOR SEQ ID NO: 5:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

Tyr Thr Arg Leu Arg Lys Gln Met Ala Val Lys Lys Tyr Leu Asn Ser
1               5                   10                  15

Ile Leu Asn (2) INFORMATION FOR SEQ ID NO: 6:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(xi) SEQUENCE DESCRIPTION: SEQ ID NO: 6:

Xaa His Trp Ser Tyr Lys Leu Arg Pro Gly
1               5                   10

(2) INFORMATION FOR SEQ ID NO: 7:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(xi) SEQUENCE DESCRIPTION: SEQ ID NO: 7:

Xaa His Tyr Ser Leu Lys Trp Lys Pro Gly
1               5                   10

(2) INFORMATION FOR SEQ ID NO: 8:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear

```
    (ii) MOLECULE TYPE: peptide (ix) FEATURE:
         (A) NAME/KEY: Modified-site
         (B) LOCATION: 1
         (D) OTHER INFORMATION: /note= "D isomer of
             2-naphthylalanine"

(ix) FEATURE:
         (A) NAME/KEY: Modified-site
         (B) LOCATION: 2
         (D) OTHER INFORMATION: /note= "D isomer of
             4-chlorophenylalanine"

(ix) FEATURE:
         (A) NAME/KEY: Modified-site
         (B) LOCATION: 3
         (D) OTHER INFORMATION: /note= "Xaa is D-Trp"

(ix) FEATURE:
         (A) NAME/KEY: Modified-site
         (B) LOCATION: 6
         (D) OTHER INFORMATION: /note= "Xaa is D-Lys"

(ix) FEATURE:
         (A) NAME/KEY: Modified-site
         (B) LOCATION: 10
         (D) OTHER INFORMATION: /note= "Xaa is D-Ala"

(xi) SEQUENCE DESCRIPTION: SEQ ID NO: 8:

Xaa Xaa Xaa Ser Arg Xaa Leu Arg Pro Xaa
1               5                   10

(2) INFORMATION FOR SEQ ID NO: 9:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Modified-site
         (B) LOCATION: 4
         (D) OTHER INFORMATION: /product= "Nle"

(ix) FEATURE:
         (A) NAME/KEY: Modified-site
         (B) LOCATION: 7
         (D) OTHER INFORMATION: /note= "Xaa is D-Phe"

(xi) SEQUENCE DESCRIPTION: SEQ ID NO: 9:

Ser Tyr Ser Xaa Asp His Xaa Arg Trp Lys
1               5                   10

(2) INFORMATION FOR SEQ ID NO: 10:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Modified-site
         (B) LOCATION: 17
         (D) OTHER INFORMATION: /product= "Nle"

(xi) SEQUENCE DESCRIPTION: SEQ ID NO: 10:
```

```
His Ser Asp Ala Val Phe Thr Glu Asn Tyr Thr Lys Leu Arg Lys Gln
1               5                   10                  15

Xaa Ala Ala Lys Lys Tyr Leu Asn Asp Leu Lys Lys Gly Gly Thr
                20                  25                  30
```

(2) INFORMATION FOR SEQ ID NO: 11:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(xi) SEQUENCE DESCRIPTION: SEQ ID NO: 11:

```
Xaa His Tyr Ser Tyr Leu Lys Trp Lys Pro Gly
1               5                   10
```

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "D isomer of
            2-naphthylalanine"

(ix) FEATURE:
        (A) NAME/KEY: Modified-site
        (B) LOCATION: 2
        (D) OTHER INFORMATION: /note= "D isomer of
            4-chlorophenylalanine"

(ix) FEATURE:
        (A) NAME/KEY: Modified-site
        (B) LOCATION: 3
        (D) OTHER INFORMATION: /note= "Xaa is D-Trp"

(ix) FEATURE:
        (A) NAME/KEY: Modified-site
        (B) LOCATION: 6
        (D) OTHER INFORMATION: /note= "Xaa is D-Lys"

(xi) SEQUENCE DESCRIPTION: SEQ ID NO: 12:

```
Xaa Xaa Xaa Ser Arg Xaa Trp Lys Pro Gly
1               5                   10
```

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1

```
            (D) OTHER INFORMATION: /note= "Xaa is pyroglutamic acid"

(ix) FEATURE:
          (A) NAME/KEY: Modified-site
          (B) LOCATION: 6
          (D) OTHER INFORMATION: /note= "Xaa is D-Lys"

(xi) SEQUENCE DESCRIPTION: SEQ ID NO: 13:

Xaa His Trp Ser Tyr Xaa Leu Arg Pro Gly
1               5                   10

(2) INFORMATION FOR SEQ ID NO: 14:

(i) SEQUENCE CHARACTERISTICS:
          (A) LENGTH: 9 amino acids
          (B) TYPE: amino acid
          (C) STRANDEDNESS: <Unknown>
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /note= "Xaa is D-Phe"

(ix) FEATURE:
          (A) NAME/KEY: Modified-site
          (B) LOCATION: 5
          (D) OTHER INFORMATION: /note= "Xaa is D-Trp"

(xi) SEQUENCE DESCRIPTION: SEQ ID NO: 14:

Lys Xaa Cys Phe Xaa Lys Thr Cys Thr
1               5

(2) INFORMATION FOR SEQ ID NO: 15:

(i) SEQUENCE CHARACTERISTICS:
          (A) LENGTH: 10 amino acids
          (B) TYPE: amino acid
          (C) STRANDEDNESS: <Unknown>
          (D) TOPOLOGY: linear (ii) MOLECULE TYPE: peptide (ix) FEATURE:
          (A) NAME/KEY: Modified-site
          (B) LOCATION: 3
          (D) OTHER INFORMATION: /note= "Xaa is D-Phe"

(ix) FEATURE:
          (A) NAME/KEY: Modified-site
          (B) LOCATION: 6
          (D) OTHER INFORMATION: /note= "Xaa is D-Trp"

(xi) SEQUENCE DESCRIPTION: SEQ ID NO: 15:

Lys Asp Xaa Cys Phe Xaa Lys Thr Cys Thr
1               5                   10

(2) INFORMATION FOR SEQ ID NO: 16:

(i) SEQUENCE CHARACTERISTICS:
          (A) LENGTH: 9 amino acids
          (B) TYPE: amino acid
          (C) STRANDEDNESS: <Unknown>
          (D) TOPOLOGY: linear (ii) MOLECULE TYPE: peptide (ix) FEATURE:
          (A) NAME/KEY: Modified-site
          (B) LOCATION: 2
          (D) OTHER INFORMATION: /note= "Xaa is D-Phe"
```

```
    (ix) FEATURE:
        (A) NAME/KEY: Modified-site
        (B) LOCATION: 5
        (D) OTHER INFORMATION: /note= "Xaa is D-Trp"

(xi) SEQUENCE DESCRIPTION: SEQ ID NO: 16:

Asp Xaa Cys Phe Xaa Lys Thr Cys Thr
1               5

(2) INFORMATION FOR SEQ ID NO: 17:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is D-Phe"

(ix) FEATURE:
        (A) NAME/KEY: Modified-site
        (B) LOCATION: 7
        (D) OTHER INFORMATION: /note= "Xaa is D-Trp"

(xi) SEQUENCE DESCRIPTION: SEQ ID NO: 17:

Lys Lys Lys Xaa Cys Phe Xaa Lys Thr Cys Thr
1               5                   10

(2) INFORMATION FOR SEQ ID NO: 18:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is D-Phe"

(ix) FEATURE:
        (A) NAME/KEY: Modified-site
        (B) LOCATION: 7
        (D) OTHER INFORMATION: /note= "Xaa is D-Trp"

(xi) SEQUENCE DESCRIPTION: SEQ ID NO: 18:

Lys Lys Asp Xaa Cys Phe Xaa Lys Thr Cys Thr
1               5                   10

(2) INFORMATION FOR SEQ ID NO: 19:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is D-Phe"
```

```
        (ix) FEATURE:
             (A) NAME/KEY: Modified-site
             (B) LOCATION: 7
             (D) OTHER INFORMATION: /note= "Xaa is D-Trp"

(xi) SEQUENCE DESCRIPTION: SEQ ID NO: 19:

Lys Asp Ser Xaa Cys Phe Xaa Lys Thr Cys Thr
1               5                  10

(2) INFORMATION FOR SEQ ID NO: 20:

(i) SEQUENCE CHARACTERISTICS:
             (A) LENGTH: 10 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 3
             (D) OTHER INFORMATION: /note= "Xaa is D-Phe"

(ix) FEATURE:
             (A) NAME/KEY: Modified-site
             (B) LOCATION: 6
             (D) OTHER INFORMATION: /note= "Xaa is D-Trp"

(xi) SEQUENCE DESCRIPTION: SEQ ID NO: 20:

Lys Asp Xaa Cys Phe Xaa Lys Thr Cys Asp
1               5                  10

(2) INFORMATION FOR SEQ ID NO: 21:

(i) SEQUENCE CHARACTERISTICS:
             (A) LENGTH: 9 amino acids
             (B) TYPE: amino acid
             (C) STRANDEDNESS: <Unknown>
             (D) TOPOLOGY: linear (ii) MOLECULE TYPE: peptide (ix) FEATURE:
             (A) NAME/KEY: Modified-site
             (B) LOCATION: 1
             (D) OTHER INFORMATION: /note= "Xaa is D-Phe"

(ix) FEATURE:
             (A) NAME/KEY: Modified-site
             (B) LOCATION: 4
             (D) OTHER INFORMATION: /note= "Xaa is D-Trp"

(xi) SEQUENCE DESCRIPTION: SEQ ID NO: 21:

Xaa Cys Phe Xaa Lys Thr Cys Thr Lys
1               5

(2) INFORMATION FOR SEQ ID NO: 22:

(i) SEQUENCE CHARACTERISTICS:
             (A) LENGTH: 31 amino acids
             (B) TYPE: amino acid
             (C) STRANDEDNESS: <Unknown>
             (D) TOPOLOGY: linear (ii) MOLECULE TYPE: peptide (xi) SEQUENCE DESCRIPTION: SEQ ID NO: 22:

Cys Gly Cys His Ser Asp Ala Val Phe Thr Asp Asn Tyr Thr Arg Leu
1               5                  10                  15

Arg Lys Gln Met Ala Val Lys Lys Tyr Leu Asn Ser Ile Leu Asn
```

-continued

```
                20              25              30
```

(2) INFORMATION FOR SEQ ID NO: 23:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

```
Cys Gly Cys Val Phe Thr Asp Asn Tyr Thr Arg Leu Arg Lys Gln Met
1               5                   10                  15

Ala Val Lys Lys Tyr Leu Asn Ser Ile Leu Asn
            20                  25
```

(2) INFORMATION FOR SEQ ID NO: 24:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(xi) SEQUENCE DESCRIPTION: SEQ ID NO: 24:

```
Xaa His Trp Ser Tyr Gly Leu Arg Pro Gly
1               5                   10
```

(2) INFORMATION FOR SEQ ID NO: 25:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "D isomer of
            2-naphthylalanine"

(ix) FEATURE:
        (A) NAME/KEY: Modified-site
        (B) LOCATION: 2
        (D) OTHER INFORMATION: /note= "D isomer of
            4-chlorophenylalanine"

(ix) FEATURE:
        (A) NAME/KEY: Modified-site
        (B) LOCATION: 3
        (D) OTHER INFORMATION: /note= "Xaa is D-Trp"

(ix) FEATURE:
        (A) NAME/KEY: Modified-site
        (B) LOCATION: 6
        (D) OTHER INFORMATION: /note= "Xaa is D-Arg"

(xi) SEQUENCE DESCRIPTION: SEQ ID NO: 25:

```
Xaa Xaa Xaa Asp Glu Xaa Leu Lys Pro
1               5
```

```
(2) INFORMATION FOR SEQ ID NO: 26:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(ix) FEATURE:
        (A) NAME/KEY: Modified-site
        (B) LOCATION: 6
        (D) OTHER INFORMATION: /note= "Xaa is D-Trp"

(xi) SEQUENCE DESCRIPTION: SEQ ID NO: 26:

Xaa His Trp Ser Lys Xaa Leu Arg Pro Gly
 1               5                  10

(2) INFORMATION FOR SEQ ID NO: 27:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(ix) FEATURE:
        (A) NAME/KEY: Modified-site
        (B) LOCATION: 6
        (D) OTHER INFORMATION: /note= "Xaa is D-Lys"

(xi) SEQUENCE DESCRIPTION: SEQ ID NO: 27:

Xaa His Tyr Ser Leu Xaa Leu Arg Pro Gly
 1               5                  10

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 28:

Ser Tyr Ser Met Glu His Phe Arg Trp Gly Lys Pro Val
 1               5                  10

(2) INFORMATION FOR SEQ ID NO: 29:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide
```

```
        (ix) FEATURE:
              (A) NAME/KEY: Modified-site
              (B) LOCATION: 4
              (D) OTHER INFORMATION: /product= "Nle"

(ix) FEATURE:
              (A) NAME/KEY: Modified-site
              (B) LOCATION: 7
              (D) OTHER INFORMATION: /note= "Xaa is D-Phe"

(ix) FEATURE:
              (A) NAME/KEY: Modified-site
              (B) LOCATION: 8
              (D) OTHER INFORMATION: /note= "Xaa is a nitrated arginine
                  residue"

(xi) SEQUENCE DESCRIPTION: SEQ ID NO: 29:

Ser Tyr Ser Xaa Asp His Xaa Xaa Trp Lys
1               5                   10

(2) INFORMATION FOR SEQ ID NO: 30:

(i) SEQUENCE CHARACTERISTICS:
              (A) LENGTH: 9 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 3
              (D) OTHER INFORMATION: /product= "Nle"

(ix) FEATURE:
              (A) NAME/KEY: Modified-site
              (B) LOCATION: 6
              (D) OTHER INFORMATION: /note= "Xaa is D-Phe"

(xi) SEQUENCE DESCRIPTION: SEQ ID NO: 30:

Gly Cys Xaa Asp His Xaa Arg Trp Lys
1               5

(2) INFORMATION FOR SEQ ID NO: 31:

(i) SEQUENCE CHARACTERISTICS:
              (A) LENGTH: 10 amino acids
              (B) TYPE: amino acid
              (C) STRANDEDNESS: <Unknown>
              (D) TOPOLOGY: linear (ii) MOLECULE TYPE: peptide (ix) FEATURE:
              (A) NAME/KEY: Modified-site
              (B) LOCATION: 4
              (D) OTHER INFORMATION: /product= "Nle"

(ix) FEATURE:
              (A) NAME/KEY: Modified-site
              (B) LOCATION: 7
              (D) OTHER INFORMATION: /note= "Xaa is D-Phe"

(xi) SEQUENCE DESCRIPTION: SEQ ID NO: 31:

Cys Gly Cys Xaa Asp His Xaa Arg Trp Lys
1               5                   10

(2) INFORMATION FOR SEQ ID NO: 32:

(i) SEQUENCE CHARACTERISTICS:
              (A) LENGTH: 28 amino acids
```

```
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 17
        (D) OTHER INFORMATION: /product= "Nle"

(xi) SEQUENCE DESCRIPTION: SEQ ID NO: 32:

His Ser Asp Ala Val Phe Thr Asp Asn Tyr Thr Lys Leu Arg Lys Gln
 1               5                  10                  15

Xaa Ala Val Lys Lys Tyr Leu Asn Ser Val Leu Thr
             20                  25

(2) INFORMATION FOR SEQ ID NO: 33:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is pyroglutamic acid"

(xi) SEQUENCE DESCRIPTION: SEQ ID NO: 33:

Xaa His Tyr Ser Leu Glu Trp Lys Pro Gly
 1               5                  10

(2) INFORMATION FOR SEQ ID NO: 34:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /note= "Xaa is D-Phe"

(ix) FEATURE:
        (A) NAME/KEY: Modified-site
        (B) LOCATION: 7
        (D) OTHER INFORMATION: /note= "Xaa is D-Trp"

(xi) SEQUENCE DESCRIPTION: SEQ ID NO: 34:

Gly Cys Asp Xaa Cys Phe Xaa Lys Thr Cys Thr
 1               5                  10
```

RADIOMETAL-BINDING PEPTIDE ANALOGUES

This application is a division of application Ser. No. 08/893,749, filed Jul. 11, 1997, now U.S. Pat. No. 6,126,916, which claims the benefit of Provisional application Ser. No. 60/021,662, filed Jul. 2, 1996.

BACKGROUND OF THE INVENTION

This invention provides derivatives of biologically useful cyclic and acyclic peptides in which one or more amino acid side chains or a segment attached to the peptide chain contain chelating moieties that can tightly bind metal ions, including radionuclides. The labeled peptides carry the metal to specific in vivo targets such as receptors and antigens, and are useful for radiodiagnostic imaging, therapy and radiotherapy. New methods for preparing the peptides are also provided.

Radiolabeled peptides are useful in the diagnosis and therapy of a variety of human disease states that are characterized by overexpression of peptide hormone receptors. Thus, for example, it has been shown that radiolabeled analogues of LHRH (luteinizing hormone releasing hormone) and somatostatin selectively bind to hormone-sensitive tumors characterized by cell-surface overexpression of LHRH hormone receptors. Similarly, peptide hormone analogues such as $^{123}$I-vasoactive intestinal peptide (VIP), $^{99m}$Tc-P829, $^{111}$In-DTPA Octreotide and $^{111}$In-bisMSH-DTPA have been used to image human tumors that over express VIP, somatostatin, somatostatin and melanocyte stimulating hormone (MSH) receptors respectively. See: Virgolini et al. *Engl. J. Med.* 169:1116 (1994); Virgolini et al. *J. Nucl. Med.* 36:1732, (1995); Lister-James et al. *Nucl. Med.*, 36, 91P, #370, 1995 meeting abstract; Pearson et al. *J. Med. Chem.* 39:1361, (1996); Krenning et al. *J. Nucl. Med.*, 33:652 (1992); and Wraight et al. *Brit. J. Radiol.* 65:112 (1992).

Many tyrosine-containing peptides may be labeled with $^{125}$I by well known methods and used for receptor binding studies. For example, the incidence of VIP receptor upregulation has been studied in vitro in a wide range of cancer types using $^{125}$I-[Tyr$^{10}$]-VIP as the radioligand. See Reubi, *Nucl. Med.* 36:1846 (1995). The VIP receptor was detected in a wide variety of cancer types, including breast, prostate, ovarian, pancreatic, endometrial, bladder, colon, esophageal, SCLC, astrocytoma, glioblastoma, meningioma, pheochromocytoma, lymphoma, neuroblastoma adenoma, and GEP tumors. An iodinated VIP analogue $^{123}$I-[Tyr$^{10}$]-VIP has also been used to image VIP receptor-rich tumors in humans. See Virgolini et al, supra.

The use of radioiodine for in vivo diagnostic and therapeutic uses has distinct disadvantages, however. $^{123}$I, the most useful isotope in vivo, is very expensive ($45.30/mCi) and must be produced in a cyclotron. This isotope, furthermore, has a half-life of only 13.2 hours, thereby requiring that it be produced in a geographic location close to where any radioiodinated imaging agent must be used. Other radioisotopes, such as $^{99m}$Tc and $^{188}$Re are preferred for diagnostic and therapeutic uses, respectively. $^{99m}$Tc, for example, is inexpensive ($0.50/mCi), is readily available (produced in a generator from $^{99}$Mo, a reactor product), and has an ideal gamma emission energy for imaging with a gamma camera.

Some peptides either directly contain, or are amenable to the introduction of, residues that allow direct binding of radiometals such as $^{99m}$Tc and $^{188}$Re to the peptide. For example, somatostatin contains a disulfide bond that, upon reduction, provides two sulfhydryl-containing cysteine side chains that can directly bind $^{99m}$Tc. See U.S. Pat. No. 5,225,180. See also WO 94/28942, WO 93/21962 and WO 94/23758. Complexes of this type tend, however, to be heterogeneous and unstable, which limits their clinical utility. Moreover, the use of free sulfhydryls in this manner limits the radiometals which can be used to label the peptide to those that tightly bind free S—H groups. This method further suffers from the problem that direct binding of the metal to an amino acid side chain can greatly influence the peptide conformation, thereby deleteriously altering the receptor binding properties of the compound.

Most peptides either do not contain a metal-binding amino acid sequence motif or, for various reasons such as those described supra, are not amenable to suitable sequence modifications that would permit introduction of such a motif. Some means of rendering the peptide capable of binding radiometals must therefore be introduced into the peptide. A preferred approach is to attach a metal binding ligand to a specified site within the peptide so that a single defined, stable, complex is formed. The ligands used to bind metals often contain a variety of heteroatoms such as nitrogen, sulfur, phosphorous, and oxygen that have a high affinity for metals.

Chelates have conventionally been attached via covalent linkages to the N-terminus of a peptide or peptide analogue, following independent synthesis of the peptide and chelate moieties. For example, Maina et al. have described the coupling of a tetra-amine chelator to the N-terminus of a somatostatin analogue, allowing $^{99m}$Tc labeling of the peptide. See *J. Nucl. Biol. Med.* 38:452 (1994). Coupling in this manner is, however, undesirable when the N-terminus of the peptide plays an important role in its receptor binding properties. Accordingly, application of this method is limited by the requirement that the N-terminus of the peptide accommodate the presence of a (usually sterically bulky) chelator without deleteriously affecting the binding properties of the peptide.

Alternatively, chelating agents have been introduced into peptide side chains by means of, site-selective reactions involving particular amino acid residues. For example, the lysine residue at position 6 of LHRH has been directly acylated with a chelating group. See Bajusz, S. et al. *Proc. Natl. Acad. Sci. USA* 86:6313 (1989). This method is inherently limited by the lack of chemical selectivity available when more than one side chain can potentially react with the chelator, or when the peptide sequence does not contain an amino acid that can be derivatized in this way. A further limitation of this approach can arise when multidentate ligands are used. A single ligand molecule can react with multiple peptide molecules resulting in the formation of significant amounts of cross-linked products.

Chelating agents have been introduced on the side chain of a peptide through tris amino-acids as described by Dunn T. J. et al. WO 94/26294. This method does not provide a method for cyclizing the peptides. The side chain protecting groups used to introduce the ligand described in this work are the same as those typically used for peptide amide cyclization. See Felix et al. *Int. J. Peptide Protein Res.* 32:441 (1988).

A fully-protected BAT (bisaminothiol) chelating agent has been synthesized and coupled to the side chain of a lysine residue, which could then be incorporated into a peptide. See Dean et al. WO 93/25244. These fully protected precursors are very time consuming, expensive and cumbersome to prepare. The difficulty and expense of preparing such precursors make this method untenable for preparing a diverse array of ligands attached to the variety of linkers that is needed to design a metal carrying targeting agent.

One potential solution to this problem is to use a protecting group strategy that allows selective coupling of a chelator moiety to specified positions within a peptide chain. The diversity of chemical reactivities present within the amino acid side chains of a peptide has, however, led to difficulties in achieving sufficient selectivity in site-specific deprotection of protecting groups. This lack of selectivity has also heretofore hampered efforts to selectively deprotect two or more different functional groups within a peptide to allow coupling of these groups in, for example, a cyclic peptide.

Edwards et al. *J. Med. Chem.* 37:3749 (1994) have disclosed a fragment method of assembling a cyclic disulfide on a resin with a subsequent attachment of an intact ligand (DTPA). This approach afforded the known somatostatin targeting agent DTPA-Octreotide. This approach was specifically designed for the preparation of a known compound. A more typical situation, however, requires that a variety of labeled peptides to optimize binding to a particular target. Such a situation requires, therefore, a broader approach allowing the assembly of multiple ligands, best assembled in fragments, placed at any point desired in a sequence which can also be cyclized at a variety of positions in the peptide sequence.

Additional considerations for the synthesis of peptides that can selectively bind metals include the effect of the chelate on the conformation of the peptide. Most peptides are highly conformationally flexible, whereas efficient receptor binding usually requires that a peptide adopt a specific conformation. Whether or not the peptide can adopt this specific conformation is greatly influenced by charge and hydrophilic/hydrophobic interactions, including the effects of a covalently attached metal chelating moiety. It is possible to enhance peptide receptor affinity and selectivity by restricting the conformations that the peptide can adopt, preferably locking the peptide into an active conformation. This is often most readily achieved by preparing cyclic peptides. Cyclic peptides have the added advantage of enhanced resistance to proteases, and therefore frequently demonstrate a longer biological half-life than a corresponding linear peptide.

Peptides can be cyclized by a variety of methods such as formation of disulfides, sulfides and, especially, lactam formation between carboxyl and amino functions of the N- and C-termini or amino acid side chains. However, the plethora of functionality within a peptide chain typically means that, for all but the shortest peptides, selective coupling between two desired functional groups within a peptide is very difficult to achieve.

It is apparent, therefore, that cyclic peptides that can chelate metals ions while retaining the ability to specifically bind with high affinity to a receptor are greatly to be desired. It is also desirable to have a means of attaching a chelating moiety to any predetermined position within a peptide, and to have a means of selectively forming cyclic peptides between any two preselected positions within a peptide chain. Additionally, it is desirable to have access to a method that would allow a chelating moiety to be coupled to a peptide at any desired stage during peptide synthesis.

SUMMARY OF THE INVENTION

It is therefore an object of the present invention to provide peptides that can bind radionuclides while retaining the ability to specifically bind to the peptide receptor. It is a further object of the invention to provide methods of preparing and radiolabeling peptides that can bind radionuclides while retaining the ability to specifically bind to the peptide receptor. It is a still further object of the invention to provide diagnostic and therapeutic methods of using the radiolabeled peptides to image or treat a tumor, an infectious lesion, a myocardial infarction, a clot, atherosclerotic plaque, or a normal organ or tissue.

In accomplishing the foregoing objects of the invention, there has been provided, in accordance with one aspect of the current invention, a peptide comprising a radiometal-binding moiety, wherein said binding moiety comprises the structure I:

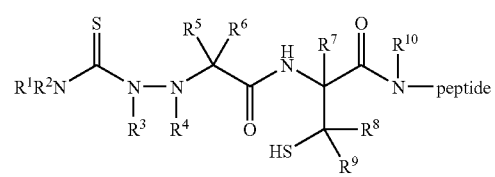

where $R^1$, $R^2$, and $R^3$ independently are selected from the group consisting of H, lower alkyl, substituted lower alkyl, cycloalkyl, substituted cycloalkyl, heterocycloalkyl, aryl, substituted aryl, heteroaryl, substituted heteroaryl, alkaryl, and a protecting group that can be removed under the conditions of peptide synthesis, provided that at least one of $R^1$, $R^2$, or $R^3$ is H. $R^4$, $R^5$, $R^6$, $R^7$, $R^8$, $R^9$ and $R^{10}$ independently are selected from the group consisting of H, lower alkyl, substituted lower alkyl, aryl, and substituted aryl, or $R^4$ and $R^6$ together optionally form a direct bond. $R^8$ and $R^9$ together or $R^7$ and $R^9$ together may form a cycloalkyl or substituted cycloalkyl ring, and $NR^{10}$ is located at the N-terminus of said peptide, or is located on an amino acid side chain of said peptide.

In preferred embodiments of the invention, $R^1$ is H, $R^3$ is H, $R^4$ is H, or $R^4$ and $R^6$ together form a direct bond. In other preferred embodiments, $R^2$ is lower alkyl or substituted or unsubstituted phenyl, or more preferably methyl or phenyl. In other preferred embodiments, $R^8$ and $R^9$ are methyl.

In accordance with another aspect of the invention, the peptides further comprise a bound metal atom. In preferred embodiments the metal atom is $^{99m}$Tc, $^{186}$Re, or $^{188}$Re.

In accordance with yet another aspect of the invention, there is provided a method of preparing a metal-chelating composition, where a solution of a peptide comprising a radiometal-binding moiety is contacted with stannous ions, where the binding moiety has the structure set forth above, followed by contacting the solution with a radionuclide, and recovering the radiolabeled peptide. In a preferred embodiment of the method the radionuclide is $^{188}$Re- or $^{186}$Re-perrhenate or $^{99}$Tc-pertechnetate.

In accordance with still another aspect of the invention, there is provided a method of imaging a tumor, an infectious lesion, a myocardial infarction, a clot, atherosclerotic plaque, or a normal organ or tissue, comprising administering to a human patient a radiolabeled peptide, together with a pharmaceutically acceptable carrier, and, after a sufficient time for said radiolabeled peptide to localize and for non-target background to clear, the site or sites of accretion of said radiolabeled peptide are detected by an external imaging camera, where the radiolabeled peptide is prepared by contacting a solution of a peptide with stannous ions, where the peptide comprises a radiometal-binding moiety having the structure set forth above, and then contacting said solution with a radionuclide and recovering the radiolabeled peptide.

In accordance with another aspect of the invention there are provided peptides having a structure selected from the group consisting of:
(Chel)γAbuNle<u>DHF</u>$_d$ <u>RWK</u>-NH$_2$, (SEQ ID NO:1)
(Chel)γAbuHSDAVFTDNYTRLRKQMAVKKYLNSILN-NH$_2$, (SEQ ID NO:2)
KPRRPYTDNYTRLRK(Chel)QMAVKKYLNSILN-NH$_2$, (SEQ ID NO:3)
(Chel)γAbuVFTDNYTRLRKQMAVKKYLNSILN-NH$_2$, (Chel)γAbuYTRLRKQMAVKKYLNSILN-NH$_2$, (SEQ ID NO:4)
HSDAVFTDNYTRLRK(Chel)QMAVKKYLNSILN-NH$_2$, (SEQ ID NO:5)
(SEQ ID NO:6)<GHWSYK(Chel)LRPG-NH$_2$, <GHYSLK(Chel)WKPG-NH$_2$, (SEQ ID NO:7)
AcNal$_d$ Cpa$_d$ W$_d$ SRK$_d$ (Chel)LRPA$_d$-NH$_2$, (SEQ ID NO:8)
(SEQ ID NO:9) (Chel)γAbuSYSNleDHF$_d$ RWK-NH$_2$, Ac-HSDAVFTENYTKLRK(Chel)QNleAAK<u>KYLND</u>LKKGGT-NH$_2$, (SEQ ID NO:10)
(SEQ ID NO:12) Nal$_d$ Cpa$_d$ W$_d$ SRK$_d$ (Chel)WKPG-NH$_2$, <GHWSYK$_d$(Chel)LRPG-NH$_2$, (SEQ ID NO:13)
(SEQ ID NO:14) AcK(Chel)F$_d$ <u>CFW</u>$_d$ <u>KTCT</u>-OH, AcK(Chel)DF$_d$ <u>CFW</u>$_d$ <u>KTCT</u>-OH, (SEQ ID NO:15)
(SEQ ID NO:14) AcK(Chel)F$_d$ <u>CFW</u>$_d$ <u>KTCT</u>-ol, AcK(Chel)DF$_d$ <u>CFW</u>$_d$ <u>KTCT</u>-ol, (SEQ ID NO:15)
(SEQ ID NO:16) (Chel)DF$_d$ <u>CFW</u>$_d$ <u>KTCT</u>-OH, K(Chel)DF$_d$ <u>CFW</u>$_d$ <u>KTCT</u>-ol, (SEQ ID NO:15)
(SEQ ID NO:17) K(Chel)KKF$_d$ <u>CFW</u>$_d$ <u>KTCT</u>-ol, K(Chel)KDF$_d$ <u>CFW</u>$_d$ <u>KTCT</u>-OH, (SEQ ID NO:18)
(SEQ ID NO:19) K(Chel)DSF$_d$ <u>CFW</u>$_d$ <u>KTCT</u>-OH, K(Chel)DF$_d$ <u>CFW</u>$_d$ <u>KTCT</u>-OH, (SEQ ID NO:15)
(SEQ ID NO:20) K(Chel)DF$_d$ <u>CFW</u>$_d$ <u>KTCD</u>-NH$_2$, K(Chel)DF$_d$ <u>CFW</u>$_d$ <u>KTCT</u>-NH$_2$, (SEQ ID NO:15)
(SEQ ID NO:18) K(Chel)KDF$_d$<u>CFW</u>$_d$<u>KTCT</u>-NHNH$_2$, AcK(Chel)F$_d$ <u>CFW</u>$_d$ <u>KTCT</u>-NHNH$_2$, (SEQ ID NO:14)
(SEQ ID NO:14) K(Chel)F$_d$ <u>CFW</u>$_d$ <u>KTCT</u>-ol, and F$_d$ <u>CFW</u>$_d$ <u>KTCT</u>K(Chel)-NH$_2$, (SEQ ID NO:21)

wherein (Chel) is a radiometal-binding moiety having the structure set forth above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The present invention provides new chelating moieties that can be covalently linked to peptides, cyclic peptides and peptide analogues. The chelating moieties allow the peptides, cyclic peptides and peptide analogues to stably bind metals, especially radiometals. Methods of preparing these chelators, peptides and peptide analogues are also provided. The peptides and peptide analogues are prepared by site-specifically introducing the metal-chelating moieties into peptides that are synthesized by solid-phase or solution phase methods. The chelating moieties may be attached to an amine-bearing side-chain of an amino acid within the peptide chain, or may be attached to the N-terminus of the peptide. Peptides according to the invention include, but are not limited to, cyclic metal-binding analogues of LHRH, vasoactive intestinal peptide (VIP), heregulins (erbB binding peptides) α, β1, β2, and β3, melanotropin (α-MSH), somatostatin, calcitonin, epidermal growth factor, gonadotrophin releasing hormone, heregulins growth hormone releasing hormone, dynorphin, calcitonin gene-related peptide, vasotocin, mesotonin, adrenocorticotropic hormone, corticotropin, gonadotropin, prolactin, vasopressin, oxytocin, substance P, substance K, and angiotensin.

The chelating moieties may be represented by the general formula I:

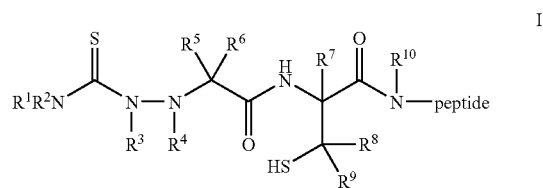

where $R^1$, $R^2$, and $R^3$ independently are selected from the group consisting of H, lower alkyl, substituted lower alkyl, cycloalkyl, substituted cycloalkyl, heterocycloalkyl, aryl, substituted aryl, heteroaryl, substituted heteroaryl, alkaryl, and a protecting group that can be removed under the conditions of peptide synthesis. At least one of $R^1$, $R^2$, or $R^3$ must be H. $R^4$, $R^5$, $R^6$, $R^7$, $R^8$, $R^9$ and $R^{10}$ independently are selected from the group consisting of H, lower alkyl, substituted lower alkyl, aryl, and substituted aryl. $R^4$ and $R^6$ together also may optionally form a direct bond, and $R^8$ and $R^9$ together or $R^7$ and $R^9$ together also may form a cycloalkyl or substituted cycloalkyl ring. $NR^{10}$ is located at the N-terminus of the peptide to which the chelator is attached, or is located on an amino acid side chain of that peptide. When $R^1$, $R^2$, $R^5$, or $R^6$ bears a heteroatom substituted function, the heteroatom also may be used to carry out additional peptide coupling reactions.

Examples of lower alkyl include, but are not limited to, straight or branched chain $C_1$–$C_6$ alkyl groups, such as a methyl, ethyl, n-propyl, i-propyl, n-butyl, i-butyl, s-butyl, t-butyl, n-pentyl, i-pentyl, and n-hexyl. Cycloalkyl includes $C_3$–$C_6$ cycloalkyl, such as cyclohexyl. Heterocycloalkyl includes tetrahydrofuran, tetrahydropyran, pyrrolidine, and piperidine. Heteroaryl includes pyrrolyl, furanyl, thienyl, imidazolyl, oxazolyl, oxazolylthio, thiazolyl, pyrazolyl pyrrolidinyl, pyridinyl, pyrimidinyl, morpholinyl, and piperizinyl. Aryl includes $C_6$–$C_{12}$ aryl such as phenyl, α-naphthyl, or β-naphthyl.

Alkaryl includes: $C_6$–$C_{12}$aryl$C_1$–$C_6$alkyl, such as phenyl$C_1$–$C_6$alkyl, or α- or β-naphthyl$C_1$–$C_6$alkyl, such as benzyl, phenylethyl, phenylpropyl, phenylbutyl, phenylpentyl, α- or β-naphthylmethyl, napthylethyl, naphthylpropyl, naphthylbutyl, or naphthylpentyl.

Examples of substituent groups include: $C_1$–$C_6$ alkoxy, for example, methoxy, ethoxy, propoxy; $C_1$–$C_6$ alkylthio, for example methylthio, ethylthio, propylthio; $C_6$–$C_{12}$aryl$C_1$–$C_6$alkoxy, for example phenyl$C_1$–$C_6$ alkoxy such as benzyloxy; aralkylthio, for example phenyl$C_1$–$C_6$alkylthio such as benzylthio; amino, substituted amino, for example $C_1$–$C_6$alkylamino such as methylamino, ethylamino; $C_6$–$C_{12}$aryl$C_1$–$C_6$alkyl, such as phenyl$C_1$–$C_6$ alkyl for example benzyl; $C_6$–$C_{12}$aryl such as phenyl; $C_3$–$C_8$ cycloalkyl such as cyclohexyl; and $C_3$–$C_8$ cycloalkyl$C_1$–$C_6$alkyl such as cyclohexylmethyl.

Preferred embodiments of the invention include compounds where $R^2$ is H, methyl, or phenyl, and where $R^8$ and $R^9$ are methyl. Other preferred embodiments are where $R^1$, $R^3$, $R^5$, $R^7$ and $R^{10}$ are H.

The peptides may be synthesized using differentially protected bis-amino acid derivatives in which either amino function can be selectively deprotected. These derivatives are introduced into a growing peptide chain during peptide synthesis by conventional peptide coupling methodology. One of the amino functions is then selectively deprotected, allowing subsequent coupling of either all or a part of a chelating molecule, or addition of further amino acid residues to continue the peptide synthesis. Peptide synthesis can be continued by coupling at the α-amino group, leading to a peptide with a conventional amide backbone, or at the side-chain amino group to produce a peptide whose amide backbone is interrupted by the side chain structure. Alternatively, the free amino function can be used to cyclize onto a reactive functionality located elsewhere in the peptide, thereby producing a cyclic peptide. Suitable bis-amino acids will be readily apparent to the skilled practitioner, and include lysine, ornithine, and 2,3-diaminopropionic acid (amino-serine). Alternatively, the chelating moiety may be introduced at the end of peptide synthesis by coupling the chelating moiety to the deprotected N-terminus of the resin-bound peptide. The chelating moiety may be added as a complete unit, in protected or unprotected form, or may be synthesized in stepwise fashion to construct the complete chelating structure.

Bis-amino acids used in the present invention may be generally represented by the formula: ZHN—CH(—R—NHY)—CO$_2$H where R is (CH$_2$)$_n$ or (CH$_2$)$_n$—X—(CH$_2$)$_n$ where X is a heteroatom such as O, S, or N and n=1–20. Alternatively the hydrogen atoms of the CH$_2$ groups can be replaced with lower alkyl, substituted lower alkyl, or alkenyl groups, or cyclic or heterocyclic rings such as cyclohexane, benzene, and piperidine, or other groups well known to the skilled artisan. The substituents Z and Y independently can be H, N, lower alkyl, substituted lower alkyl, aryl, or substituted aryl.

If peptide synthesis is continued, selective deprotection of the second amino group of the bis-amino acid can be accomplished at any point during the peptide synthesis to introduce the chelating moiety. The complete chelating moiety can be synthesized prior to coupling to the peptide, or it can be synthesized by sequentially coupling segments to the peptide. Once assembly of the entire peptide/chelator structure is complete, cleavage, deprotection, and purification affords the desired peptide derivative. This derivative is then labeled with a radiometal for use in radiodiagnostic and radiotherapeutic applications.

Alternatively, if all or part of the chelating molecule is coupled to the deprotected amino group first, the second step is to deprotect the other amino group and continue with the peptide synthesis. If only part of the chelator moiety is coupled to the peptide at this stage, the synthesis of the chelator can be finished at any point during or after synthesis of the peptide chain by appropriate deprotection and coupling reactions. Final cleavage, deprotection and purification steps once again yield the pure peptide derivative, which is then radiolabeled as before.

Attachment of the chelator to the peptide prior to cleavage from the resin results in reduced formation of cross-linked products even when multidentate activated chelators such as DTPA-dianhydride are used.

Preparation of cyclic peptides is achieved by selective deprotection of two compatible functional moieties at specified positions of the peptide sequence, followed by cyclization between the compatible moieties. Cyclization can be achieved between any two points of the peptide sequence, including between the N- and C-termini, between a terminus and an internal functional group within the peptide sequence, or between two internal functional groups. Cyclization can be achieved using either solution-phase or solid-phase peptide syntheses, but is preferably carried out using solid-phase techniques.

The deprotection and cyclization can be carried out at any point during the synthesis of the peptide prior to the final deprotection reactions. For example, the entire protected peptide sequence can be prepared prior to the cyclization, or the cyclization can be carried out on a protected peptide intermediate, followed by completion of the synthesis. Similarly, the cyclization can be carried out either before or after all or part of the metal chelating moiety is coupled to the peptide. Use of a photocleavable or other resin known to those skilled in the art on a solid phase peptide synthesizer also allows release of a protected peptide from a solid support, with subsequent solution phase selective deprotection and cyclization. Alternatively, the side chains to be cyclized can be selectively deprotected prior to cleavage from the resin, and the cyclization carried out in solution phase.

Reactions involving the C-terminus of the peptide, including but not limited to cyclization reactions, may be accomplished through the release of a protected peptide from the resin in the manner described above. Alternatively, the growing peptide chain may be attached to the resin via the side chain of a residue and the C-terminal carboxyl group suitably protected. When a reaction with the C-terminal carboxyl group is desired, it is selectively deprotected and the reaction allowed to proceed. In the case of cyclization reactions, the deprotection of the C-terminus can be accomplished before, during, or after the selective deprotection of the compatible reactive group.

The radiometal chelating peptides of the present invention stably retain radionuclide in blood and other bodily fluids and tissues. Both the reagents and the conditions in the present method are greatly simplified over those in the prior art, and the labeled peptides are particularly suitable for radiodiagnostic and radiotherapy applications using technetium or rhenium labeling.

The approach outlined above allows the placement of a radiometal-binding moiety anywhere in a peptide sequence. Placing the chelating moiety on an amino acid side-chain, either directly or via a spacer group, rather than on the N-terminus of a peptide, has the added advantage of spatially distancing the metal complex from the peptide backbone, thereby minimizing the effect of the metal complex on the peptide conformation. This also allows the N-terminus of the peptide to be used for cyclizing the peptide, if necessary.

It is known that peptide conformation is greatly influenced by charge and hydrophilic/hydrophobic interactions, and it is therefore important to consider these variables when designing a chelating ligand to be used in peptides. It is preferred that a variety of chelating complexes of varying charge and hydrophilicity and containing spacer groups of various lengths are prepared and tested to select the metal-complexed peptide that displays the optimum combination of target selectivity, pharmacokinetics, and chelate stability. The skilled artisan will appreciate that such testing is routine in the art.

The radiolabeled peptides of the present invention bind specifically to a diseased cell or tissue that exhibits both a high receptor density and high affinity for the peptide. The radioactivity of the radionuclide allows diagnosis and/or treatment of the tumor or diseased tissue. The invention also includes pharmaceutical compositions comprising an effective amount of at least one of the radiolabeled peptides of the invention, in combination with a pharmaceutically acceptable sterile vehicle, as described, for example, in Remington's Pharmaceutical Sciences; Drug Receptors and Receptor Theory, 18th ed., Mack Publishing Co., Easton, Pa. (1990). The invention also includes kits for labeling peptides which are convenient and easy to use in a clinical environment.

A. Design and Synthesis of Linear Peptides Incorporating Chelating Moieties (i) In General The peptides of the invention contain radiometal-chelating amino acid derivatives that are characterized by the presence of at least one thiol or thiocarbonyl group, and at least one nitrogen present as either a tertiary amine, a hydrazone, or a secondary amide or hydrazide. The sulfur and nitrogen atoms are suitably disposed to form a multidentate ligand capable of tightly and preferentially binding a metal ion. The multidentate ligand may also contain a spacer group that serves to separate the chelated metal from the rest of the peptide. The metal ion is preferably a reduced radionuclide, and in a preferred embodiment is $^{99m}$Tc, $^{186}$Re, or $^{188}$Re.

The invention also provides a method for placing ligands for other metals at any point in a peptide sequence. These ligands can be introduced intact, for example DTPA, or as fragments. In this way ligands for other metals of medical interest including, but not limited to, In, Ga, Y, Cu, Pt, Mn, Gd, Au, Ag, Hg, and Lu can be placed in a peptide targeting sequence.

The method allows the introduction of any metal chelate or chelate fragment that is suitably protected for peptide synthesis. The method also provides a method for the introduction of base-sensitive ligand derivatives that can be placed at any point in the peptide sequence as long as it is introduced at the end of the synthesis. An example is the synthesis of a ligand attached to the side chain of lysine using the following ligand fragment Trityl-S—COCH$_2$N(Boc)CH$_2$CO$_2$H. The S-Trityl ester will be sensitive towards base so it would not be possible to place this ligand fragment on the peptide at an earlier point in the synthesis.

Each of the chelating moieties of the invention can be prepared by methods well known to the skilled practitioner in the art of organic synthesis. The chelating moieties are constructed from subunits that are linked together by simple coupling or condensation reactions, such as the condensation of an amino, hydrazino, or hydrazido function with an activated carboxyl group, coupling of hydrazines with aldehydes, or reductive amination reactions between amines and aldehydes. As used herein the term "condensation" is intended to encompass reactions that couple together subunits of the chelating moiety, and thus encompasses reactions such as reductive amination in addition to reactions that conform to the classical definition of a condensation reaction.

Following a condensation reaction, additional functional groups on the subunit may be deprotected to allow additional condensation reactions. For example, a second subunit carrying a free carboxyl group and a protected amino function can be condensed with an amino, hydrazino, or hydrazido function on a first subunit to produce a larger, suitably protected fragment of the metal binding ligand. The amino function on the second subunit moiety can then be deprotected and further coupled to a third subunit. As used herein, the term "fragment" is intended to encompass a subunit or assembly of subunits comprising all or part of the metal binding ligand.

Methods of activating carboxyl groups for such condensation reactions are well known to those of skill in the art of organic synthesis and peptide synthesis, and include the use of active esters and of carbodiimide and phosphoryl azide coupling agents. Suitable protecting groups are used for protecting functions on the subunits when the reactivity of the functions is incompatible with a reaction used to join the subunits or with reactions used for synthesis of the peptide chain. Protecting groups for mercapto, amino and carboxylic acid functions are well known in the art. See, for example, Greene, PROTECTIVE GROUPS IN ORGANIC SYNTHESIS (Wiley Interscience, N.Y., 1981). The subunits used to construct the chelate are either readily prepared by methods well known in the art, or are commercially available from suppliers such as Advanced ChemTech (Lexington, Ky.), Milligen (Burlington, Mass.), Applied Biosystems (Foster City, Calif.), or Aldrich Chemical Corp. (Milwaukee, Wis.).

The condensation reactions used to link together the chelator subunits can either be carried out prior to peptide synthesis, or during synthesis of the peptide sequence. When the amino acid derivative is assembled from its subunits prior to peptide synthesis, α-amino and α-carboxyl functions must be suitably protected in a manner that is subsequently compatible with selective deprotection and activation of these functionalities for peptide synthesis. Examples of such protecting groups are well known in the art, and include the fluorenemethyloxycarbonyl (Fmoc), benzyloxycarbonyl (Cbz), $^t$butoxycarbonyl (Boc), allyloxycarbonyl (aloc), 4-methoxytrityl (mtt), and 1-(4,4-dimethyl-2,6-dioxocyclohex-1-ylidene)ethyl (Dde) groups for amino protection. Groups for carboxyl protection include the methyl (Me), benzyl (Bn), $^t$butyl ($^t$Bu), and allyl esters, respectively.

The amino and carboxyl protecting groups must be selected such that each group can be selectively deprotected in the presence of the other. Such protecting moieties are said to be orthogonal. The requirement that orthogonal protecting groups be used precludes, for example, use of the CBZ group for protection of the amino function in the presence of a carboxyl group protected as a benzyl ester. See Greene, supra. In a preferred embodiment the α-amino group is protected as an Fmoc group, and the α-carboxyl group is a methyl ester. The thiol protecting group used in the compounds of the invention can be any organic or inorganic group which is readily removed under mild conditions to regenerate the free sulfhydryl in the presence of the peptide without substantially altering the activity of the protein. Suitable protecting groups are listed in Greene, supra, pp. 193–217. Examples of suitable protecting groups include substituted and unsubstituted trityl groups, thiol esters, thiocarbamates and disulfides. In a preferred embodiment the thiol protecting group is a trityl group or a 4-methoxytrityl group. Those skilled in the art are familiar with the procedures of protecting and deprotecting thiol groups. For example, benzoate thioesters may be deprotected under mild and selective conditions using hydroxylamine. Once assembly of the protected chelating moiety is complete, the α-carboxy function is deprotected and coupled to the amino terminus of the peptide chain using conventional methods of peptide synthesis. See, Bodanszky et al., THE PRACTICE OF PEPTIDE SYNTHESIS (Springer Verlag, Heidelberg, 1984).

When the metal-chelating amino acid derivative is assembled from its subunits during peptide synthesis, the peptide chain is assembled by conventional solution phase or, preferably, solid phase synthesis until the point where the derivative is to be incorporated. The differentially protected bis-amino acid is then coupled to the amino terminus of the peptide chain. Subsequent selective deprotection of one of the amino groups of the derivative allows either peptide synthesis or chelator synthesis to continue.

If the α-amino function is deprotected first, all or part of the remaining amino acid residues are then coupled to the peptide chain in the conventional manner. The side chain amino function of the derivative is then deprotected, and the chelating moiety is assembled as described above. The complete peptide can then be deprotected and purified by standard methods.

If the side chain amino function is deprotected first, all or part of the chelating moiety is then assembled as described above, followed by deprotection of the α-amino group. Peptide synthesis is completed in the conventional manner as described above.

Once peptide synthesis is complete the fully protected peptide is deprotected and purified. Methods for deprotection and purification of synthetic peptides are well known in the art. See, for example, Bodanszky, supra. If the peptide was synthesized by solid phase techniques the peptide must also be cleaved from the resin used as the solid support for the synthesis. Methods for achieving this cleavage also are well known in the art. Methods for purifying synthetic peptides such as those of the present invention also are well known to those of skill in the art. Such methods include, for example, ion exchange, gel filtration chromatography, and reversed phase high pressure liquid chromatography (RP-HPLC). In a preferred embodiment of the invention the peptide is purified by RP-HPLC using a preparative-scale octadecylsilane (C18) silica column packing, eluting with a gradient of acetonitrile in 0.1% trifluoroacetic acid (TFA). The purity of the peptide can be confirmed by standard methods such as analytical RP-HPLC or capillary electrophoresis. The identity of the peptide can be confirmed by NMR spectroscopy or, in a preferred embodiment of the invention, by mass spectrometry.

As noted above, it is important that the chelating moiety does not interfere with peptide binding to the appropriate receptor. Determining the residues within the peptide that can be replaced without deleteriously affecting receptor binding can be carried out in a systematic and straightforward way by preparing a series of peptides in which each successive residue is replaced with, for example, alanine, (an "alanine scan"). The alanine-substituted peptides then are screened for biological activity. Modern peptide synthesizers make synthesis of peptides in this way quite straightforward, and screening of a large number of peptides is routine for the skilled artisan. Retention of high receptor binding affinity in a peptide containing such an alanine substitution denotes that the substituted amino acid is less important for receptor binding, and indicates a position where the metal-binding residue may be placed. Synthesis of peptides wherein a chelator is placed in each of these positions is then straightforward, and routine screening establishes the optimal position for the chelator.

As set forth above, a wide variety of peptides containing metal binding ligands may be prepared using the methods of the present invention. Additional methods of preparing metal chelating peptides using the methods of the claimed invention will be apparent to the skilled artisan. Specific applications using these methods are set forth below to further-exemplify the invention, but it will be appreciated that these examples are merely illustrative and are not meant to limit the scope of application of the invention.

(ii) Preparation of Chelating Moieties

In a preferred embodiment, the chelator contains a thiol group together with a thiosemicarbazide or thiosemicarbazone group, and can be represented by the general formula I:

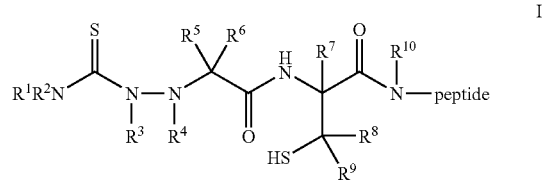

where $R^1$, $R^2$, and $R^3$ independently are selected from the group consisting of H, lower alkyl, substituted lower alkyl, cycloalkyl, substituted cycloalkyl, heterocycloalkyl, aryl, substituted aryl, heteroaryl, substituted heteroaryl, alkaryl, and a protecting group that can be removed under the conditions of peptide synthesis. At least one of $R^1$, $R^2$, or $R^3$ must be H. $R^4$, $R^5$, $R^6$, $R^7$, $R^8$, $R^9$ and $R^{10}$ independently are selected from the group consisting of H, lower alkyl, substituted lower alkyl, aryl, and substituted aryl. $R^4$ and $R^6$ together also may optionally form a direct bond, and $R^8$ and $R^9$ together or $R^7$ and $R^9$ together also may form a cycloalkyl or substituted cycloalkyl ring. $NR^{10}$ is located at the N-terminus of the peptide to which the chelator is attached, or is located on an amino acid side chain of that peptide. When $R^1$, $R^2$, $R^5$, or $R^6$ bears a heteroatom substituted function, the heteroatom also may be used to carry out additional peptide coupling reactions.

Although an understanding of the mechanism of metal binding by the chelating moieties is not necessary for practicing the invention, and without wishing to be bound by any theory, it is believed that the metal is bound to the chelator via the two sulfur atoms plus two nitrogen atoms. It is hypothesized that the metal-binding nitrogens are the α-nitrogen of the β-thiol-containing amino acid and the thiocarbazide/thiocarbazone nitrogen distal to the thiocarbonyl group. When the metal is reduced radioperrhenate or reduced radiopertechnetate, the two sulfur and two nitrogen atoms provide four coordination positions on the metal.

These compounds may be prepared by methods that are well known in the art of organic synthesis. Thus, for example, compounds having formula I may be prepared by amide coupling between an α-carboxyl-protected amino acid moiety having a protected or unprotected β-thiol-containing side chain (a "cysteine-type amino acid"), and a carboxyl-containing thiosemicarbazone or thiosemicarbazide moiety. This coupling can be carried out using well-known methods, such as carbodiimide-mediated coupling. Deprotection of the α-carboxyl group of the amino acid allows amide coupling of the chelating moiety to an amino side chain, or the amino terminus, of the peptide. Alternatively, an N- and S-protected cysteine-type amino acid having a β-thiol containing side chain may first be coupled to the peptide, followed by N-deprotection and amide coupling to a carboxyl-containing thiosemicarbazone or thiosemicarbazide moiety.

Cysteine-type amino acids may be prepared by standard methods of amino acid synthesis. The configuration at the α-carbon may be (R) or (S), or the amino acid may be racemic. Similarly, the configuration at the β-carbon, when asymmetrically substituted may be (R), (S), or (R/S). The amino acid is protected for subsequent coupling reactions using standard methods.

Thiosemicarbazones may be prepared by the condensation of semicarbazides with carbonyl compounds. Reduction of the thiosemicarbazones with, for example, sodium borohydride, provides substituted thiosemicarbazides. In a preferred embodiment, a thiosemicarbazide is reacted with glyoxylic acid to form the corresponding thiosemicarbazone, which optionally may be reduced to form a substituted thiosemicarbazide.

Many thiosemicarbazides are commercially available from, for example, Aldrich Chemical Company, Milwaukee, Wis. Other thiosemicarbazides may be prepared by the reaction of a hydrazine with, for example, an isothiocyanate. Asymmetrically substituted hydrazines also are commercially available, or may be prepared by nitrosation of amines to the nitrosamine, followed by reduction to the hydrazine. Isothiocyanates may be prepared by reaction of an amine with thiophosgene. Other methods of preparing thiosemicarbazides are well known to the skilled artisan.

In some instances, it is found that thiosemicarbazides have low solubility in the solvents used for coupling to the cysteine-like amino acid. In such instances, the coupling can be carried out using the thiosemicarbazone, followed by coupling to the peptide. The thiosemicarbazone then may be reduced to the thiosemicarbazide using sodium borohydride or another suitable reducing agent. When the thiosemicarbazide is sufficiently soluble to be used directly, the α-nitrogen must first be protected prior to coupling. Suitable protecting groups are well known in the art and include Boc and Cbz groups.

(iii) Linear VIP Receptor Targeting Agents

Naturally occurring VIP has the sequence:

HSDAVFTDNYTRLRKQMAVKKYLNSILN-NH$_2$(SEQ ID NO:2)

An alanine scan has revealed several residues whose replacement with alanine does not greatly affect receptor binding. These residues include Lys-15, Gln-16, Val-19, Lys-21, Asn-24, Ser-25 and the N- and C-termini. These locations are possible sites for the attachment of a metal binding ligand according to the present invention.

Chelating derivatives based on attachment of the metal binding ligand at these positions include, but are not limited to, those with a metal binding moiety attached, either directly or via a spacer group, to the pharmacophore via the side chain amine of a lysine or other bis-amino acid residue. Specific chelating derivatives of this general structure include, but are not limited to:

MaGCγAbuHSDAVFTDNYTRLRKQMAVKKYLNSILN-NH$_2$ (SEQ ID NO:2)

AcCGCHSDAVFTDNYTRLRKQMAVKKYLNSILN-NH$_2$ (SEQ ID NO:22)

KPRRPYTDNYTRLRK(PtscGC)QMAVKKYLNSILN-NH$_2$ (SEQ ID NO:3)

MaGCγAbuVFTDNYTRLRKQMAVKKYLNSILN-NH$_2$ (SEQ ID NO:4)

AcCGCVFTDNYTRLRKQMAVKKYLNSILN-NH$_2$ (SEQ ID NO:23)

MaGCγAbuYTRLRKQMAVKKYLNSILN-NH$_2$ (SEQ ID NO:5)

HSDAVFTDNYTRLRK(PtscGC)QMAVKKYLNSILN-NH$_2$ (SEQ ID NO:2)

HSDAVFTDNYTRLRK(Dtpa)QMAVKKYLNSILN-NH$_2$ (SEQ ID NO:2)

HSDAVFTDNYTRLRK(AGC)QMAVKKYLNSILN-NH$_2$ (SEQ ID NO:2)

where Ma is mercaptoacetic acid,

PtscG is 2-(4-phenyl-3-thiosemicarbazidyl)acetic acid or PhNHCSNHNHCH$_2$CO$_2$H, γAbu is γ-aminobutyric acid, and in K(PtscGC), the parentheses denote that enclosed amino acids are attached to the epsilon. amine of lysine and the first amino acid attached is C followed by PtscG.

In each of the compounds described above, the chelating moiety may be replaced by a chelator of the general formula I, as described above.

(iv) Linear LHRH Receptor Targeting Agents

Naturally occurring LHRH has the sequence:

<GHWSYGLRPG-NH$_2$ (SEQ ID NO:24)

where <G is pyroglutamic acid. It is further known that the bicyclic peptide AcNal$_d$ Cpa$_d$ W$_d$ (cyclo4–10)D(cyclo5–8) ER$_d$ LKPDap-NH$_2$ (SEQ ID NO:25) (where W$_d$ indicates that the D isomer of the amino acid was used, Nal is 2-naphthylalanine, Cpa is 4-chlorophenylalanine and Dap is 2,3-diaminopropionic acid) binds to the LHRH receptor. See Bienstock et al. *J. Med. Chem.* 36:3265 (1993). It is also known that the side chain of position 6 of LHRH is very bulk tolerant. See Barbacci et al. *J. Biol. Chem.* 270:9585 (1995). This location is a possible site for the attachment of a metal binding ligand according to the present invention.

Linear chelating derivatives based on attachment of the metal binding ligand at this position include, but are not limited to, those with a metal binding moiety attached, either directly or via a spacer group, to the pharmacophore via the side chain amine of a lysine or other bis-amino acid residue. Specific linear chelating derivatives of these general structures include, but are not limited to:

<GHWSYK(MaGC)LRPG-NH$_2$ (SEQ ID NO:6)
<GHYSLK(MaGC)WKPG-NH$_2$ (SEQ ID NO:7)
<GHWSYK(Ma-azaGC)LRPG-NH$_2$ (SEQ ID NO:6)
<GHYSLK(PtscGC)WKPG-NH$_2$ (SEQ ID NO:7)
<GHYSLK(PtscGDap)WKPG-NH$_2$ (SEQ ID NO:7)
<GHWSYK$_d$(MaGC)LRPG-NH$_2$ (SEQ ID NO:13)
<GHYSLK(azaGGC)WKPG-NH$_2$ (SEQ ID NO:7)
<GHWSYK(iECG)LRPG-NH$_2$ (SEQ ID NO:6)
<GHWSYK$_d$(MtaGC$_a$)LRPG-NH$_2$ (SEQ ID NO:13)
<GHYSLK(iECiD)WKPG-NH$_2$ (SEQ ID NO:7)
<GHYSLK(DiGlyGDap)WKPG-NH$_2$ (SEQ ID NO:7)
<GHYSLK(iDGDap)WKPG-NH$_2$ (SEQ ID NO:7)
<GHWSYK(MtaGC)LRPG-NH$_2$ (SEQ ID NO:6)
<GHWSK(MaGC)W$_d$LRPG-NH$_2$ (SEQ ID NO:26)
<GHWSYK$_d$ (MtaGDap)LRPG-NH$_2$ (SEQ ID NO:13)
<GHWSYK$_d$ (PtscGC)LRPG-NH$_2$ (SEQ ID NO:13)
<GHWSYK$_d$ (E)LRPG-NH$_2$ (SEQ ID NO:13)
<GHWSYK$_d$ (MtscGC)LRPG-NH$_2$ (SEQ ID NO:13)
<GHWSYK$_d$ (Mta(hqss)GDap)LPG-NH$_2$ (SEQ ID NO:8)
AcNal$_d$ Cpa$_d$ W$_d$ SRK$_d$ (MaGC)LRPA$_d$-NH$_2$ (SEQ ID NO:8)
Nal$_d$ Cpa$_d$ W$_d$ SRK$_d$ (PtscGC)LRPA$_d$-NH$_2$ (SEQ ID NO:8)
AcNal$_d$Cpa$_d$ W$_d$SRK$_d$(MaFC)LRPA$_d$-NH$_2$ (SEQ ID NO:8)
AcNal$_d$ Cpa$_d$ W$_d$ SRK$_d$ (azaGFC)LRPA$_d$-NH$_2$ (SEQ ID NO:6)

where:

<G is pyroglutamic acid,

Ma is mercaptoacetic acid azaG is azaglycine or H$_2$NNHCH$_2$ CO$_2$H,

PtscG is 2-(4-phenyl-3-thiosemicarbazidyl)acetic acid or PhNHCSNHNHCH$_2$CO$_2$H, Dap is 2,3-diaminopropionic acid iD is an aspartic acid coupled via the side chain carboxyl group,
iE is a glutamic acid coupled via the side chain acid group,
DiGly is HOOCCH$_2$ NHCH$_d$ COO—,
Mta(hqss) is S-(2,5-dihydroxyphenyl-S-methyl) sulfoniumacetyl
C$_a$ is an Acm protected cysteine
Mta is the methylthioether of mercaptoacetic acid,
Nal is 2-naphthylalanine,
Cpa is 4-chlorophenylalanine,
in K$_d$, the subscript d denotes that the D isomer was used, and
in K(MaGC), the parentheses denote that enclosed amino acids are attached to the ε amine of lysine and the first amino acid attached is C followed by G and ending in Ma.

Additionally, complexes of these peptides with non-radioactive metals may be prepared. Such complexes include:

<GHWSYK(MaGC)LRPG-NH$_2$ ReO
<GHYSLK(MaGC)WKPG-NH$_2$ ReO (SEQ ID NO:7)
<GHYSLK$_d$(MaGC)LRPG-NH$_2$ReO (SEQ ID NO:27)

In each of the compounds described above, the chelating moiety may be replaced by a chelator of the general formula I, as described above.

(v) Linear α-MSH Receptor Targeting Agents

Naturally occurring α-MSH has the sequence:
Ac-SYSMEHFRWGKPV-NH$_2$ (SEQ ID NO:28).

It had previously been shown that the cyclic peptide Nle DHF$_d$ RWK-NH$_2$ (SEQ ID NO:1) (where Nle is norleucine and F$_d$ indicates D-Phe) has a high affinity for the α-MSH receptor and is known to be relatively stable in-vivo. See Al-Obeidi et al. *J. Amer. Chem. Soc.* 111:3413 (1989); Haskell-Luevano et al. *J. Med. Chem.* 39:432 (1996). The underlined portion indicates those residues within the cyclized portion of the peptide, and also the termini of the cyclic structure, i.e. the peptide is cyclized by an amide bond from the side chains of aspartic acid and lysine.

Linear chelating derivatives based upon the structures of these known α-MSH receptor binding peptides include those with a chelating derivative attached to the N-terminus of the peptide, either directly or via a spacer group, such as γ-amino butyric acid (γ-Abu). Specific linear chelating derivatives with this general structure include, but are not limited to:

MaGCγAbuSYSNleDHF$_d$ RWK-NH$_2$, (SEQ ID NO:9) and
MaGCγAbuSYSNleDHF$_d$ R$_n$ WK-NH$_2$ (SEQ ID NO:29)

where γ-Abu is γ-aminobutyric acid and R$_n$ is a nitrated arginine residue.

In each of the compounds described above, the chelating moiety may be replaced by a chelator of the general formula I, as described above.

B. Design and Synthesis of Cyclic Peptides Incorporating Chelating Amino Acid Derivatives (i) In General The process of preparing a cyclic metal-chelator/peptide complex is analogous to that described above for linear peptides, except that at some point during or subsequent to synthesis of the peptide chain cyclization is carried out. The cyclization can be between any two functional groups on the peptide such as the peptide termini or amino acid side chains. The cyclization can be achieved by disulfide or sulfide formation, or preferably by lactam formation. Site-selective cyclization requires selective deprotection of two functional groups on the peptide. For lactam formation this requires using an amino and a carboxyl protecting group that can be deprotected in the presence of other amino and carboxyl protecting groups. This task is made more difficult when the peptide synthesis also requires that selective deprotection be achieved between these other protecting groups. Accordingly, such a sophisticated protecting group strategy has heretofore proved difficult to achieve in practice.

The methods of the present invention allow both cyclization and coupling of the chelator moiety to the peptide to be achieved at any point during peptide synthesis. Use of appropriate protecting groups allows synthesis of the peptide, assembly of the ligand and cyclization of the peptide to be achieved in any order that is desired. This approach is more efficient than either solid-phase methods which cyclize the peptide off the resin or methods that attach ligands in solution following synthesis of the cyclic peptide.

The methods of the present invention may be used in solution phase, but preferably are carried-out using an automated solid-phase peptide synthesizer. Using a multi-well automated synthesizer allows a large number of peptides, differing in the point of attachment of the chelator moiety or in the site of cyclization, to be prepared simultaneously. These so-called "combinatorial libraries," wherein the ligand containing peptides are deprotected while still attached to the solid support, can be reacted with the appropriate-metal to form complexes and then screened in an appropriate bioactivity assay to select the compound having the optimally desired characteristics of receptor binding and stability.

Combinatorial synthesis can be carried out in "split" syntheses or by "parallel" syntheses. In split synthesis, synthetic peptide intermediates bound to beads are subdivided into different groups for addition of the next amino acid in each successive step. After each step the beads are divided into different groups for the next reaction. In parallel synthesis, different compounds are synthesized in different reactions vessels, such as the wells of a peptide synthesizer. Split synthesis provides small quantities of large numbers of compounds, whereas parallel synthesis provides larger quantities of a smaller number of compounds.

Combinatorial synthesis also requires that each individual compound be labeled in some way in order that it might be identified in the screening step. Various means of labeling compounds for this purpose are known in the art. For example, inert halogenated aromatic compounds are used as labels that can be identified by gas chromatography. See Borman, *Chem. Eng. News* 74:29 (1996) which is hereby incorporated herein in its entirety.

In a preferred embodiment of the invention cyclization is achieved by lactam formation. Most preferably the amino function is protected using an aloc group, and the carboxyl function is protected as an allyl ester. This allows simultaneous deprotection of the amino and carboxy functions using Pd(PPh$_3$)$_4$ in the presence of a nucleophile for the allyl group. The nucleophile typically used is tri-n-butyl tin hydride ("Bu$_3$SnH).

Prior to the present invention it was known that amines would react with allyl ions under Pd$^0$ catalysis. See, for example, Roos et al., *J. Org. Chem.* 60:1733 (1995) and Heck, PALLADIUM REAGENTS IN ORGANIC SYNTHESES, Academic Press, 1995, pp. 122–131. The present inventors found that this caused a problem for simultaneous deprotection of allyl-protected amino and carboxyl functions because of the side reaction wherein the newly deprotected amino function was alkylated with the allyl group. It was found, however, that addition of piperidine as an allyl scavenger during the Pd-catalyzed aloc cleavage reaction inhibited this unwanted side-reaction. This allowed deprotection of, for example, aspartic acid and lysine side chains selectively and simultaneously while greatly reducing formation of the undesired N$^\epsilon$-allyl lysine. Those skilled in the art will recognize that other primary or secondary amines will also be suitable allyl scavengers.

This method is useful and advantageous because it is compatible with Fmoc based peptide synthesis. It allows preparation of cyclic peptides on HMP and PAM resins where both the Boc or Fmoc side chain protection can be used in addition to Aloc side chain protection. This technique furthermore allows synthesis of cyclic peptides containing a metal-binding ligand attached to the side chain of an amino acid at any point in a peptide chain. Thus three orthogonal nitrogen protecting groups are used: one for building the peptide chain, such as Fmoc or Boc; a second for attaching a metal-binding ligand to a side chain of a bisaminoacid such as 4-methyltrityl(mtt) or 1-(4,4-dimethyl-2,6-dioxocyclohex-1-ylidene)ethyl (Dde); and a third, such as Aloc, for achieving side-chain to side-chain cyclization. Other protecting groups, such as Boc, Cbz, $^t$Bu and benzyl groups can be used for protection of other side-chain amino and carboy functions that are not deprotected until the peptide synthesis is finished. Combinations of these protecting groups allow the use of Rink, Wang, Merrifield, PAM and HMP-type resins for solid-phase peptide synthesis.

Cleavage of the peptides from the resin can be accomplished with trifluoroacetic acid (for Fmoc-based syntheses) or HF or trimethylsilyl trifluoromethanesulfonate (for Boc-based syntheses).

The cyclic peptides of the invention are from 4 to 100 residues long, and have up to 5 metal chelating groups. The peptides can contain cyclized regions that are between 2 and 60 amino acids in length, and can contain more than one cyclic portion.

Cyclization is preferably between amino and carboxy amino acid side chains to form lactam bridges, but may also be between a side chain amine and the carboxy terminus to form a lactam bridge, between a side chain acid and the N-terminal amine to form lactam, between thiols to form disulfide bridges, between hydrazines and esters to form hydrazides, between hydrazines and aldehydes to from hydrazones, between a thiol and a suitable leaving group to form a sulfide, or between a hydroxyl group and another suitable leaving group to form an ether. When more than one cyclic region is present in the compound, the bridges in the cyclic regions may be of the same or different types.

When a cyclic disulfide is to be formed, the peptide of interest is preferably synthesized using Acm protection on thiols and aloc protection on amino side chains. The aloc is cleaved and the chelating ligand is coupled to the peptide. The Acm group is then cleaved and the disulfide cyclized using thallium trifluoroacetate. Alternatively, the thiols can be protected using S-trityl groups, and the cyclization can be carried out in solution after cleavage from the resin.

Preparation of a cyclic sulfide may be achieved by, for example, cyclization of a thiol onto an α-haloamido function present on an amine side chain. Thus, for example, the peptide may be synthesized with Fmoc protection on the N-terminus and S-trityl protection on the thiol. An aloc-protected lysine side chain is then deprotected and the chelator is coupled to the lysine as described above. The Fmoc is cleaved and reacted with chloroacetyl chloride or an equivalent reagent. If an acid stable resin such as the photocleavable BromoWang resin, Wang, *J. Org. Chem.* 41:3258 (1976), is used the thiol protecting group is removed and the peptide is cyclized on the resin.

Cyclic sulfides between side chain residues are prepared by using a suitable protecting group on the N-terminus of the peptide that allows selective deprotection at two differentially protected amino side chains. For example, the N-terminus can be protected as an acetyl or Boc group, and the side chains can be protected as Fmoc and aloc groups. Following peptide synthesis, one amino acid side chain (for example, Fmoc) is selectively deprotected and coupled with the chelate moiety as described above. Another amino side chain (for example aloc or Dde) is then deprotected and coupled to a sulfide electrophile such as haloacetyl or maleimide. The protecting group on the sulfur of interest is cleaved and cyclization is carried out on the resin using a base catalyst. Alternatively, the peptide can be cleaved and the cyclization can be carried out in solution. As set forth above, a wide variety of cyclic peptides may be prepared using the methods of the present invention. Additional methods of preparing cyclic metal chelating peptides using the methods of the claimed invention will be apparent to the skilled artisan. Specific applications using these methods are set forth below to further exemplify the invention, but it will be appreciated that these examples are merely illustrative and are not meant to limit the scope of application of the invention.

(ii) Cyclic α-MSH Receptor Targeting Agents

Naturally occurring α-MSH has the sequence Ac-SYS-MEHFRWGKPV-NH$_2$ (SEQ ID NO:28). It had previously been shown that the cyclic peptide Nle<u>DHF$_d$ RWK</u>-NH$_2$ (SEQ ID NO:1) (where Nle is norleucine and F$_d$ indicates D-Phe) has a high affinity for the α-MSH receptor and is known to be relatively stable in-vivo. See Al-Obeidi et al. *J. Amer. Chem. Soc.* 111:3413 (1989); Haskell-Luevano et al. *J. Med. Chem.* 39:432 (1996). The underlined portion indicates those residues within the cyclized portion of the peptide, and also the termini of the cyclic structure, i.e. the peptide is cyclized by an amide bond from the side chains of aspartic acid and lysine. This cyclic structure is used as a basis for constructing labeled peptides according to the present invention.

Cyclic chelating derivatives based upon the structure of the known α-MSH receptor binding ligand include those with a chelating derivative attached to the N-terminus of the peptide, either directly or via a spacer group, such as γ-amino butyric acid (γ-Abu). Specific chelating derivatives of this general structure include, but are not limited to:

MaGCγAbuNle<u>DHF$_d$ RWK</u>-NH$_2$ (SEQ ID NO:1)
PtscGCNle<u>DHF$_d$ RWK</u>-NH$_2$ (SEQ ID NO:30)
AcCGCNle<u>DHF$_d$ RWK</u>-NH$_2$ (SEQ ID NO:31)
DTPA-Nle<u>DHF$_d$ RWK</u>-NH$_2$ (SEQ ID NO:1)
where
Ma is mercaptoacetic acid,
γAbu is γ-aminobutyric acid,
PtscG is 2-(4-phenyl-3-thiosemicarbazidyl)acetic acid, and
DTPA is diethylenetriaminepentaacetic acid.

In each of the compounds described above, the chelating moiety may be replaced by a chelator of the general formula I, as described above.

(iii) Cyclic VIP R ceptor Targeting Agents

Naturally occurring VIP has the sequence:

HSDAVFTDNYTRLRKQMAVKKYLNSILN-NH$_2$ (SEQ ID NO:2)

Native VIP is thought to form a helical structure in solution. See Musso et al. *Biochemistry* 27:8174 (1988). The putative helix structure can be stabilized by intramolecular cyclization via the side chains of residues placed in spatial proximity by the helical structure. Examples include:

Ac-HSDAVFTENYTKLRKQNleAAK
KYLNDLKKGGT-NH$_2$ (SEQ ID NO:10)
Ac-HSDAVFTDNYTKLRKQNleAVKKYLNSVLT-NH$_2$
(SEQ ID NO:32)

(where Nle is norleucine). See O'Donnell et al. *J. Pharm. Exp. Ther.* 270:1282; U.S. Pat. No. 4,822,890; Bolin, Eur. Pat. Appl. 0 536 741 A2. The underlined portion indicates the residues within the cyclized portion of the peptide, and also the termini of the cyclized portion, i.e. the peptide is cyclized via the formation of an amide bond between the side chains of the aspartic acid and the lysine. These cyclic structures are used as a basis for constructing labeled peptides according to the present invention.

Cyclic chelating derivatives based on these structures include, but are not limited to, those with a metal binding moiety attached, either directly or via a spacer group, to the pharmacophore via the side chain amine of a lysine or other bis-amino acid residue. Specific chelating derivatives of this general structure include, but are not limited to:

Ac-HSDAVFTENYTKLRK(PtscGC)QNleAAK
KYLNDLKKGGT-NH$_2$ (SEQ ID NO:10) (where PtscG=2-(4-phenyl-3-thioseinicarbazidyl)acetic acid); and
Ac-HSDAVFTENYTKLRK(DPTA)QNleAAK
KYLNDLKKGGT-NH$_2$ (SEQ ID NO:10) (where DTPA=diethylenetriaminepentaacetic acid).

In each of the compounds described above, the chelating moiety may be replaced by a chelator of the general formula I, as described above.

The present invention, thus generally described, will be understood more readily by reference to the following examples, which are provided by way of illustration and are not intended to be limiting of the present invention.

EXAMPLES

Example 1

Synthesis of N$^\alpha$Alloc-N$^\epsilon$-Fmoc-L-Lysine

N$^\epsilon$-Fmoc-L-Lysine (10.00 g, 27.1 mmol, 100 mol %, Bachem Biosciences, Inc.) was suspended in dioxane (100 ml) and Na$_2$CO$_3$ (1M, 33 ml) to form a milky suspension. Allyl chloroformate (3.2 ml, 30.2 mmol, 111 mol %) was added to dioxane (10 ml) and this solution was added dropwise to the suspension of N$^\epsilon$-Fmoc-L-Lysine over 10 min. Sodium carbonate, (1M, 20 ml) was added in two portions and an additional quantity of allyl chloroformate (0.3 ml) was added. The reaction was stirred at room temperature for 16 hours. The volatile solvents were removed under reduced pressure and the residue was washed with diethyl ether (50 ml). The residual liquid was then acidified with HCl (1M) and extracted with ethyl acetate (2×150 ml). The organic layers were combined, washed with saturated NaCl (50 ml), dried over Na$_2$SO$_4$, evaporated under reduced pressure to obtain a crude oily product (16 g). The crude product was dissolved in ether (100 ml) and a white solid formed and was removed by filtration. The solvent from the filtrate was removed under reduced pressure to afford a viscous pale yellow oil (8.34 g, 68% yield) which eventually formed a glassy solid.

Example 2

Synthesis of 2-(triphenylmethylmercapto) acetyl hydrazide 2-(triphenylmethylmercapto) acetic acid (20.35° g, 60.9 mmol, 100 mol %) was dissolved in anhydrous THF (150 ml) and cooled in an ice water bath. t-Butylcarbazate (8.61 g, 65.1 mmol, 107 mol %) was added to the reaction solution followed by diisopropylcarbodiimide (10.0 ml, 63.9 mmol, 105 mol %). The reaction was allowed to warm slowly to room temperature and stirred for 28 hours. The reaction mixture was filtered to remove the white precipitate that had formed and the filtrate was concentrated to a white foam by removal of the solvent under reduced pressure. This material was dissolved in chloroform (75 ml). Then acetic acid (75 ml) was added followed by the addition of borontrifluoride etherate (10.0 ml, 81 mmol, 134 mol %). The reaction was stirred at room temperature for 6 hours and then quenched by pouring the reaction mixture into water (200 ml) containing sodium acetate (30 g). This mixture was extracted with chloroform (2×100 ml). The organic layers were combined, washed with saturated NaCl solution (150 ml), dried over Na$_2$SO$_4$ and filtered. The solvent was removed under reduced pressure to obtain a pale gold oil which solidified on standing. The solid was suspended in 1:1 diethylether/hexanes (200 ml) and collected by filtration. The solid was washed with an additional quantity of 1:1 diethylether/hexanes (100 ml) and dried to afford the desired product (15.44 g, 73% yield) having ESMS MH$^+$ calculated 349, observed 349.

Example 3

Synthesis of N$^\beta$-[2-(triphenylmethylthio) acetyl]azaglycine

Glyoxylic acid monohydrate (0.59 g, 6.41 mmol, 110 mol %) was dissolved in methanol (20 ml) and 2-(triphenylmethylmercapto)acetyl hydrazide (2.03 g, 5.82 mmol, 100 mol %) was added. Dioxane (20 ml) was added to the cloudy reaction mixture and the reaction was stirred at room temperature for 18 hours. Sodium borohydride (1.76 g) was added to the reaction mixture and after 30 minutes, another quantity of sodium borohydride (0.60 g) was added. The reaction was stirred for 3 hours at room temperature, then quenched by pouring the reaction mixture into HCl (1M, 60 ml). The mixture was extracted with ethyl acetate (2×50 ml). The organic layers were combined, washed with saturated NaCl solution (40 ml), dried over Na$_2$SO$_4$, filtered, and concentrated under reduced pressure on the rotary evaporator to afford a solid (2.5 g) having ESMS MH$^+$ calculated 407, found 407.

Example 4

Synthesis of N$^\alpha$-Boc-N$^\beta$-[2-(triphenylmethylthio) acetyl] azaglycine N$^\beta$-[2-(triphenylmethylthio)acetyl]azaglycine (2.39 g, 5.89 mmol, 100 mol %) was dissolved in dioxane (50 ml). Di-t-butyl dicarbonate (BOC)$_2$O, (2.07 g, 9.48 mmol, 161 mol %) was added to the reaction solution followed by the addition of $Na_2CO_3$ (1M, 15 ml). This mixture was stirred at room temperature for 15 minutes, then additional quantities of $Na_2CO_3$ (1M, 10 ml) and $(BOC)_2O$ (1.41 g) were added. The solution was stirred at room temperature for 18 hours then reacted with NaOH (6M, 3 ml) and $(BOC)_2O$ (1.4 g) for 1 hour. The crude reaction mixture was then acidified to pH 3 with citric acid (1M) and extracted with ethyl acetate (200 ml). The organic layer was washed with saturated sodium chloride solution (60 ml), dried over $Na_2SO_4$, filtered and concentrated under reduced pressure to obtain the crude product. The crude product was dissolved in ether and diluted to obtain a 1:1 mixture with hexanes causing a white precipitate to form. The white solid was collected by filtration to obtain the desired product (1.48 g, 50% yield) having ESMS $MH^+$ calculated 507, found 507.

Example 5

Synthesis of 2-(4-Phenyl-3thiosemicarbazidyl)acetic acid

4-Phenyl-3-thiosemicarbazide (6.02 g, 36 mmol, 100 μmol %) was suspended in methanol (40 ml). Glyoxylic acid monohydrate (3.32 g, 36.1 mmol, 100 mol %) was added and the reaction was stirred at room temperature for 2 hours. Sodium borohydride (1.50 g) was added carefully, and the reaction mixture bubbled-very vigorously. The reaction mixture was stirred at room temperature for 1 hour, then $NaBH_4$ (0.66 g) was added, followed by the addition of glacial acetic acid (6 ml). After 15 minutes, $NaBH_4$ (1.08 g) was added, and the reaction was stirred at room temperature for 15 hours. An additional quantity of $NaBH_4$ (1.66 g) was then added and the reaction was stirred at room temperature for 3 hours, before it was quenched with HCl (1M, 200 ml). The mixture was then extracted with ethyl acetate (2×150 ml). The organic layers were combined, washed with saturated NaCl solution (100 ml), dried over $Na_2SO_4$, filtered, and the solvent removed under reduced pressure to afford a yellow solid (9.03 g) having ESMS Negative ion mode $M-H^+$ Calculated 224 Found 224.

Example 6

Synthesis of $N^\beta$-Boc-2-(4-Phenyl-3-thiosemicarbazidyl)acetic acid 2-(4-Phenyl-3-thiosemicarbazidyl)acetic acid (8.93 g, 37.9 mmol, 100 mol %) and $(BOC)_2O$ (9.10° g) were dissolved in dioxane (100 ml). Sodium carbonate (1M, 50 ml) and water (50 ml) were added and the mixture was stirred at room temperature for 5 hours. Sodium hydroxide (1M, 40 ml) and an additional quantity of $(BOC)_2O$ (6.21 g), were added and the reaction was stirred overnight at room temperature. The reaction was quenched with citric acid (1M) and extracted with ethyl acetate (2×100 ml). The organic layers were combined, washed with saturated NaCl (50 ml), dried over $Na_2SO_4$, and filtered. The filtrate was concentrated under reduced pressure to afford a gummy solid (19 g). The crude solid was suspended in ether and a white solid was collected by filtration. The solid was washed with ether (100 ml) to obtain the desired product (3.17 g) having ESMS $MH^+$ calculated 326, found 326.

Example 7

Synthesis of $N^\alpha$-(triphenylmethylsulfenyl)-$N^\beta$-(Boc) azaglycine $^t$-Butylcarbazate was condensed with glyoxylic acid monohydrate in methanol. This crude hydrazone was then reduced by catalytic hydrogenation over 10% Pd/C. This product was then mixed with dioxane and base and a dioxane solution of triphenylmethanesulfenylchloride was added dropwise. The desired $N^\alpha$-(triphenylmethylsulfenyl)-$N^\beta$-(Boc) azaglycine (25 g) was obtained on work-up.

Example 8

Solid Phase Peptide Synthesis of Peptides Using Alloc and Fmoc Protecting Groups Solid phase peptide synthesis was carried out on a 0.050 mmol scale using an Advanced ChemTech model 348 peptide synthesizer modified to operate under nitrogen pressure in the same manner as the model 396. The allyloxycarbonyl (aloc) and 9-fluorenylmethyloxycarbonyl (Fmoc) groups were employed for nitrogen protection and diisopropylcarbodiimide (DIC)/hydroxybenzotriazole (HOBT) were used to activate the carboxyl groups for coupling. A variety of resins were used such as Rink, Pal, and TentaGel S RAM for C-terminal amides and Wang, 2-chlorotrityl, or TentaGel S PHB for C-terminal acids.

To allow either introduction of the metal binding chelate moiety and/or to allow cyclization via selectively deprotected amino acid side chains a differentially protected bis-amino acid was used for the peptide synthesis. The differentially protected bis-amino acid derivatives chosen were α-Aloc-Lys(ε-Fmoc)OH and α-Fmoc-Lys(ε-Aloc)OH. The α-Aloc-Lys(ε-Fmoc)OH derivative allowed the ligand pieces to be introduced on the side chain using a routine Fmoc procedure.

The aloc groups were cleaved on the machine in the manual mode by washing the resin bound peptide with dichloromethane (3×2 ml portions) and then mixing the resin with a solution (2 ml) containing tetrakistriphenylphosphine palladium [0] (10 mg), and acetic acid (0.1 ml). Tributyltinhydride (0.3 ml) was then added and the mixture was vortexed for one hour. The reaction cell was then emptied, the resin was washed with dichloromethane (3×2 ml) and standard Fmoc synthesis was then resumed. The peptides were cleaved from the resin with a solution of trifluoroacetic acid (TFA), anisole and ethane dithiol for 1 to 3 hours in the ratio 23:3:1. The crude cleavage mixture was then poured into ether to precipitate the crude peptide which was then purified by reverse phase HPLC using a Waters Delta. Pak, Prep Pak C-18 cartridge system eluted with an appropriate gradient of TFA (0.1%) in water and/or TFA (0.1%) in acetonitrile (90%) and water (10%). The fractions containing the desired purified peptides were collected and the volatile solvents were removed under reduced pressure to obtain the aqueous solutions of the peptides which were then lyophilized. Samples of the lyophilized products were then sent for electrospray (ESMS) or fast atom bombardment (FABMS) to confirm that the observed mass of the products matched the calculated mass of the desired peptide.

The table below shows some of the peptide sequences synthesized by the methods described above.

| Peptide | HPLC[a] | MW[b] |
|---|---|---|
| <GHWSYGLRPG—NH₂ (SEQ ID NO:24) | 6.1 | 1183 |
| <GHYSLEWKPG—NH₂ (SEQ ID NO:33) | 6.2 | 1227 |
| HSDAVFTDNYTRLRKQMAVKKYLNSILN—NH₂ (SEQ ID NO:2) | 6.7 | 3326 |
| MaGCγAbuHSDAVFTDNYTRLRKQMAVKKYLNSILN—NH₂ (SEQ ID NO:2) | 7.3 | 3645 |
| MaGCγAbUVFTDNYTRLRKQMAVKKYLNSILN—NH₂ (SEQ ID NO:4) | 7.5 | 3235 |
| MaGCγAbuNleDHFR$_d$ WK—NH2[c] (SEQ ID NO:1) | 7.0 | 1302 |
| <GHWSYK(MaGC)LRPG—NH₂ (SEQ ID NO:6) | 6.3 | 1488 |
| <GHYSLK(MaGC)WKPG—NH₂ (SEQ ID NO:7) | 6.3 | 1460 |
| <GHWSYK(Ma-azaGC)LRPG—NH₂ (SEQ ID NO:6) | 6.1 | 1503 |
| <GHYSLK(PtscGC)WKPG—NH₂ (SEQ ID NO:7) | 6.9 | 1536 |
| AcNal$_d$ Cpa$_d$ W$_d$ SRK$_d$ (MaGC)LRPA$_d$ —NH₂ (SEQ ID NO:8) | 8.2 | 1668 |
| <GHYSYLK(PtscGDap)WKPG—NH₂ (SEQ ID NO:11) | 6.6 | 1519 |
| <GHYSLK(azaGGC)WKPG—NH₂ (SEQ ID NO:7) | 6.5 | 1474 |
| Nal$_d$ Cpa$_d$ W$_d$ SRK$_d$ (PtscGC)WKPG—NH₂ (SEQ ID NO:12) | 8.1 | 1701 |
| <GHWSYK$_d$ (MaGC)LRPG—NH₂ (SEQ ID NO:13) | 6.3 | 1488 |
| AcNal$_d$ Cpa$_d$ W$_d$ SRK$_d$ (AzaGFC)LRPA$_d$ —NH₂ (SEQ ID NO:8) | | |
| AcNal$_d$ Cpa$_d$ W$_d$ SRK$_d$ (MaFC)LRPA$_d$ —NH₂ (SEQ ID NO:8) | | |
| AcNal$_d$ Cpa$_d$ W$_d$ SRK$_d$ (PtscGC)LRPA$_d$ —NH₂ (SEQ ID NO:8) | | |
| <GHWSYK(iDGDap)LRPG—NH₂ (SEQ ID NO:6) | | |
| <GHWSYK(iECG)LRPG—NH₂ (SEQ ID NO:9) | | |

[a]HPLC Method [retention time in minutes] Solvent A is 0.1% trifluoroacetic acid in water, Solvent B is 0.1% trifluoroacetic acid in 90:10 acetonitrile/water. Solvent flow rate is 3 ml/min for 10 min, then 5 ml/min for 5 min. Gradient is 0 to 100% B over 10 min then 100% B for 5 min
[b]Electrospray mass spectrum values (MH⁺)
[c]The underlined sequence is cyclized as the cyclic amide connecting the side chain functional groups
Abbreviations used in Table:
<G: pyroglutamic acid
PtscG: 2-(4-phenyl-3-thiosemicarbazidyl)acetic acid or PhNHCSNHNHCH₂CO₂H
Ma: mercaptoacetic acid
azaG: azaglycine or H₂NNHCH₂CO₂H
Dap: 2,3-diaminopropionic acid
γAbu: γ-aminobutyric acid
Nal: 2-naphthylalanine
Cpa: 4-chlorophenylalanine
K$_d$: the subscript d denotes that the D isomer was used
K(MaGC): the parentheses denote that enclosed amino acids are attached to the ε amine of lysine and the first amino acid attached is C followed by G and ending in Ma
iD: isoaspartic acid
iE: isoglutamic acid

| Sequence | MH+ | HPLC RT |
|---|---|---|
| AcK(TscGC)F$_d$CFW$_d$KTCT-OH (SEQ ID NO:14) | 1436 | 7.7 |
| AcK(TscGC)DF$_d$CFW$_d$KTCT-OH (SEQ ID NO:15) | 1552 | 7.4 |
| TscGCDF$_d$CFW$_d$KTCT-OH (SEQ ID NO:34) | 1381 | 7.7 |
| AcK(TscGC)F$_d$CFW$_d$KTCT-ol (SEQ ID NO:14) | 1422 | 7.6 |
| AcK(MtscGC)F$_d$CFW$_d$KTCT-ol (SEQ ID NO:14) | 1436 | 7.8 |
| AcK(TscGC)DF$_d$CFW$_d$KTCT-ol (SEQ ID NO:15) | 1537 | 7.4 |
| AcK(MaGG)F$_d$CFW$_d$KTCT-ol (SEQ ID NO:14) | 1378 | 7.4 |
| K(TscGC)DF$_d$CFW$_d$KTCT-NH₂ (SEQ ID NO:15) | 1508 | 7.1 |
| K(TscGC)KF$_d$CFW$_d$KTCT-ol (SEQ ID NO:17) | 1651 | 7.2 |
| K(TscGC)KDF$_d$CFW$_d$KTCT-OH (SEQ ID NO:18) | 1637 | 7.3 |
| K(TscGC)DF$_d$CFW$_d$KTCT-ol (SEQ ID NO:15) | 1495 | 7.2 |
| K(TscGC)DSF$_d$CFW$_d$KTCT-OH (SEQ ID NO:19) | 1596 | 7.4 |
| K(TscGC)DF$_d$CFW$_d$KTCT-OH (SEQ ID NO:15) | 1508 | 7.2 |
| K(TscGC)DF$_d$CFW$_d$KTCD-NH₂ (SEQ ID NO:20) | 1521 | 7.1 |
| K(TscGC)KDF$_d$CFW$_d$KTCT-NHNH (SEQ ID NO:18) | 1651 | 7.2 |
| AcK(TscGC)F$_d$CFW$_d$KTCT-NHNH₂ (SEQ ID NO:14) | 1450 | 7.4 |
| K(AGC)F$_d$CFW$_d$KTCT-ol (SEQ ID NO:14) | 1379 | 6.8 |
| AcK(TscGC)DF$_d$CFW$_d$KTCT-ol (SEQ ID NO:15) | 1537 | 7.4 |
| F$_d$CFW$_d$KTCTK(TscGC)-NH₂ (SEQ ID NO:21) | 1393 | 6.8 |

The underlined portion of the sequence is cyclic.
TscG is 3-thiosemicarbazonylglyoxyl, i.e. H₂NCSNHNCHCO—
MtscG is 4-methyl-3-thiosemicarbazonylglyoxyl, i.e. CH₃NHCSNHNCHCO—
Ma is mercaptoacetyl: HSCH₂CO—
Groups listed within parentheses are attached to the side chain of the amino acid to the left of the parentheses

Example 9

Preparation of a Cyclic MSH Analogue Containing a Chelating Moiety

The method of synthesizing cyclic peptides was demonstrated by preparing the cyclic α-melanocyte stimulating hormone (αMSH) analogue MaGCγ-AbuNleDHF$_d$RWK-NH₂, (SEQ ID NO:1) where the underlining indicates that the peptide sequence is cyclized as a lactam through the aspartic acid and lysine side chains. The residues to be used for cyclization were side-chain protected as the aloc group (for lysine) and as the allyl ester (for aspartate). The peptide was assembled using Fmoc chemistry as described above, on a polystyrene-based Rink amide resin.

Allyl and aloc deprotection was first carried out using Pd(PPh₃)₄, acetic acid, and Bu₃SnH in the absence of piperidine as an allyl scavenger. After cleavage of the side chain protecting groups, the resin was washed and the partially protected peptide was cyclized using the method described by Felix et al., Int. J. Peptide Protein Res. 32:441 (1988). The peptide was then cleaved from the resin and purified to isolate the N-allyl substituted cyclic amide as the only clean peptide from the product mixture.

The aloc cleavage reaction was then modified by the addition of piperidine as an allyl scavenger.

When the aloc and allyl groups were cleaved using a mixture containing 0.5 ml glacial acetic acid, 10 ml dichloromethane, 0.0563 g tetrakis(triphenylphosphine)palladium (0), plus 1.0 ml piperidine as an allyl scavenger. Each well on the peptide synthesizer contained 0.05 mmol of peptide on Rink resin, and was treated with 0.3 ml/well tributyltin hydride at room temperature for 1 hr with vortex mixing. The resin was washed with: 2×2 ml/well dichloromethane, 2×1 ml/well methanol, 2×1 ml/well diisopropylethyl amine, and 3×1 ml/well NMP after the cleavage of the side chain protecting groups. The peptide side chains were then coupled by the method of Felix supra (15 hr, using BOP and DIEA). The peptide was cleaved and purified as described above to afford a pure peptide with the desired ESMS MH$^+$ of 1302. The N-allylated side product was observed in only trace amounts.

Example 10

Radiolabeling with $^{99m}$Tc

A Glucoscan (DuPont) vial was reconstituted with 2.18 mCi of NaTcO$_4$ in 1 ml saline to form the $^{99m}$Tc-gluceptate complex. <GHWSYK(MaGC)LRPG amide (SEQ ID NO:6) (IMP3) was prepared as above 99m Tc-IMP$_3$ was prepared by mixing 360 μl (874 uCi) of $^{99m}$Tc-gluceptate with 640 μl of peptide in saline. The initially formed precipitate disappeared upon heating for 15 min at 75.degree°. An instant TLC (ITLC) strip developed in H$_2$O:EtOH:NH$_4$OH mixture (5:2:1) showed 6.2% of the activity at the origin as colloids. HPLC showed 100% of the activity bound to the peptide with a RT of 6.95 min, whereas the unlabeled peptide eluted at 6.4 min under the same HPLC conditions (reversed phase C-18 column, gradient of 0–100% B in 10 min at a flow rate of 3 ml/min, where A is 0.1% TFA in H$_2$O and B is 90% CH$_3$CN, 0.1% TFA). Recovery from the HPLC column was 85% of the injected activity.

IMP3 was formulated and lyophilized for $^{99m}$Tc labeling in the amounts shown below:

|   | IMP3 (μg) | Sn (μg) | αDG/SN |
|---|---|---|---|
| 1. | 250 | 23 | 14 |
| 2. | 100 | 23 | 14 |
| 3. | 250 | 15 | 14 | where αDG is α-D-glucoheptonate. The lyophilized vials were reconstituted with ~900 μμCi of NaTcO$_4$ in saline. Cloudiness was observed in all the vials. The vials were heated for 15 min at 75° C., but turbidity persisted. ITLC analysis for colloids showed 14, 21 and 9% colloids at the origin for vials 1, 2, and 3, respectively.

In order to prevent the precipitation during $^{99m}$Tc labeling, α-D-glucoheptonate (αDG) and tartrate ratios to Sn(II) were varied in the lyophilized vials. The following vials were formulated and lyophilized (250 μg of IMP3 with 25 μg Sn(II)) with tartrate and αDG ratios as shown below. The vials were reconstituted with ~500 μCi of NaTcO4 in 1 ml saline. Observations are indicated in the observation column. ITLC strips were developed after 15 min at room temperature following heating at 75° C. for 15 min.

|   | tartrate/Sn | pH | Observation | colloid, RT | colloid, 75° C. |
|---|---|---|---|---|---|
| 1. | 50 | 5.3 | ppt | | |
| 2. | 100 | 5.3 | ppt | | |
| 3. | 500 | 5.3 | ppt clears upon mixing | 17% | 2.4% |
|   | αDG/Sn | pH | Observation | colloid, RT | colloid, 75° C. |
| 4. | 25 | 5.3 | ppt | | |
| 5. | 50 | 5.3 | ppt | | |
| 6. | 100 | 5.3 | turbid | | |
| 7. | 500 | 5.3 | slight turbidity | 25% | 3.5% |
| 8. | 1000 | 5.3 | clear | 3.3% | 3.1% |

The protocol above was repeated for vials 3, 7 and 8 and colloids were determined to be 5.3, 3.8, and 4.6%, respectively after heating 15 min at 75° C. A single broad peak was observed on a reversed HPLC column at a RT of 7 min.

Solubility of peptides that are poorly soluble in saline alone is increased by the addition of a solubilizing agent such as ethanol or 2-hydroxypropyl-βcyclodextrin.

Results from labeling other peptides with technetium-99 are shown in the table below:

| Peptide | HPLC retention time[a] | HPLC retention time[b] |
|---|---|---|
| MaGCγAbuHSDAVFTDNYTRLRKQMAVKKYLNSILN—NH$_2$ (SEQ ID NO:2) | 7.62 (99%) | 7.65 |
| MaGCγAbuVFTDNYTRLRKQMAVKKYLNSILN—NH$_2$ (SEQ ID NO:4) | 7.8–9.7[c] | 8.19[c] (99%) |
| <GHWSYK(MaGC)LRPG.amide (SEQ ID NO:6) | 6.59 (95%) | 6.90[c] (92%) |
| <GHYSLK(MaGC)WKPG.amide (SEQ ID NO:7) | NA | 7.07 (100%) |
| <GHWSYK(Ma-azaGC)LRPG.amide (SEQ ID NO:6) | 6.82 (100%) | 7.02[c] (99%) |
| <GHYSLK(Ptsc-GC)WKPG.amide (SEQ ID NO:7) | 7.60 (100%) | 7.67[d] (100%) |
| AcNal$_d$ Cpa$_d$ W$_d$ SRK$_d$ (MaGC)LRPA$_d$ —NH$_2$ (SEQ ID NO:8) | 8.50 (27%) 9.00 (68%) | |
| <GHWSYK$_d$ (MaGC)LRPG—NH$_2$ (SEQ ID NO:13) | 6.83 (95%) | 7.07[c] (95%) |
| <GHYSYLK(PtscGDap)WKPG—NH$_2$ (SEQ ID NO:11) | 7.08 (96%) | 6–8[e] (90%) |

-continued

| Peptide | HPLC retention time[a] | HPLC retention time[b] |
|---|---|---|
| <GHYSLK(azaGGC)WKPG—NH$_2$ (SEQ ID NO:7) | 6.60 (100%) | 6.47[c] (99%) |
| Nal$_d$ Cpa$_d$ W$_d$ SRK$_d$ (PtscGC)WKPG—NH$_d$ (SEQ ID NO:12) | 8.43 (97%) | |

Abbreviations used in the table are the same as in Example 8 supra. A change in HPLC retention time of the complex formed by labeling at room temperature and that formed by heating indicates a change in the binding of the metal.
[a]room temperature reaction 15 min [retention time in minutes]
[b]after heating in boiling water 15 min
[c]significant change in peak shape and retention after heating
[d]no change in peak shape and retention time difference is not significant
[e]many peaks In an alternative labeling method, dilute solutions (30 μg/mL) of the peptide were formulated into labeling kits prior to addition of pertechnetate. The final solution contained the peptide, 10% hydroxypropyl-βcyclodextrin (HPCD), 200 mM glucoheptonate 21 mM acetate buffer at pH 5.3, 2 mg of ascorbic acid and 100 μg of stannous chloride in 1.5 mL total volume. In other formulations, two equivalents of stannous ion relative to the peptide were added, in a buffer containing 15% HPCD, 200 mM glucoheptonate, and 21 mM acetate buffer at pH 5.6.

Example 11

Radiolabeling of IMP-3 $^{188}$Re

IMP3, (<GHWSYK(MaGC)LRPG amide) (SEQ ID NO:6) was synthesized as above. IMP3 has a retention time of 6.4 min on a reversed phase C-18 column using a gradient of 0–100% B in 10 min at a flow rate of 3 ml/min where A is 0.1% TFA in H$_2$O and B is 90% CH$_3$ CN, 0.1% TFA.

IMP3 was formulated in 1 mg and 250 μg amounts with 450 μg Sn(II) and α-D-glucoheptonate at a ratio of 1:17.5, and lyophilized. The lyophilized vials of IMP3 (1 mg and 250 μg) were reconstituted with 617 and 578 μCi of NaReO$_4$ in saline. The vials were heated for 15 min at 75° C. HPLC analysis under the conditions described above showed single peaks at RT of 7.0 min for both vials. The effluent was collected and counted on a γ-counter. For the 1 mg vial, the recovery of activity was 88% whereas the recovery was 77% for the 250 μg vial. Colloid analyses on an ITLC strip developed in H$_2$O:EtOH:NH$_4$OH(5:2:1) showed 1.4 and 1.2% of the activity at the origin for 1 mg and 250 μg vials, respectively.

$^{188}$Re labeling at room temperature did not proceed as well as at 75° C. At room temperature, only a few percent of the activity (<5%) was incorporated into the peptide and the rest of the activity eluted in the void volume (1.2 min).

Example 12

In vitro Receptor Binding Assays

The human breast adenocarcinoma cell lines MCF-7, SK-BR-3, and MDA-MB-231 were used for testing radiometal labeled LHRH analogues. HT29 cells were used for testing labeled VIP analogues. All cells lines were purchased from the American Type Culture Collection, Rockville, Md. Cells were grown in DMEM supplemented with 5% fetal bovine serum, 5% defined equine serum, penicillin (100 U/ml), streptomycin (100 μg/ml), and L-glutamine (2 mM). The cells were routinely passaged after detachment with trypsin and 0.2% EDTA.

Specificity of the unlabeled LHRH analogue peptides is determined by competitive cell binding assay. Target cells are washed with fresh medium, and adjusted to 5×10$^5$ cell/ml. 100 μl of the cell suspension (100 μl) is added per well to a 96-well microtiter plate. The cells are allowed to attach and are then treated with different concentrations of the peptides in the presence of $^{125}$I-LHRH (Amersham Life Science, Arlington Heights, Ill., 2,000 Ci/mmol). Following a 2 h incubation at room temperature with shaking, the cells are washed twice and the radioactivity associated with the cells is counted and the concentration of the peptides that cause 50% inhibition on the binding of the labeled LH-RH is compared.

To determine receptor binding constants, serial dilutions of radiolabeled LHRH are incubated with 5×10$^5$ cells in a 96-well plate. All assay are performed in triplicates both with or without a high concentration of unlabeled LHRH to allow determination of specifically bound peptide. After a 2 h incubation at room temperature, the cells are washed and counted. The equilibrium association constant, K$_a$, and the total number of receptor sites per cell are determined by Scatchard analysis.

For testing VIP analogues and their metal complexes the protocol described Virgolini et al. (*Cancer Res.* 54:690 (1994)) is used. Briefly, $^{125}$I VIP is mixed with increasing concentrations of test peptide in a solution of binding buffer, following which each solution is added to HT29 cells in a 48 well culture plate. Each concentration is tested in triplicate. The cells are incubated at 4° C. for 2 h, followed by three washes with ice-cold binding buffer. The cells are then lysed with 2M NaOH for 5 min and the liquid in the well is removed with a cotton swab. The activity on the cotton swab is counted using a gamma counter.

The invention has been disclosed broadly and illustrated in reference to representative embodiments described above. Those skilled in the art will recognize that various modifications can be made to the present invention without departing from the spirit and scope thereof. Subject matter relating to radiometal-binding peptides also is described in copending U.S. application Ser. No. 08/474,555, the disclosure of which is hereby incorporated by reference in its entirety.

What is claimed is:

1. A method of treating a tumor, comprising administering to a human patient a radiolabeled peptide and a pharmaceutically acceptable carrier, wherein said peptide comprises a radiometal-binding moiety comprising the structure:

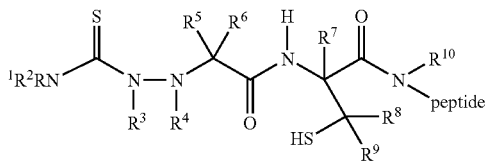

wherein $R^1$, $R^2$, and $R^3$ independently are selected from the group consisting of H, $C_1$–$C_6$ alkyl, substituted $C_1$–$C_6$ alkyl, $C_3$–$C_6$ cycloalkyl, substituted $C_3$–$C_6$ cycloalkyl, heterocycloalkyl, $C_6$–$C_{12}$ aryl, $C_6$–$C_{12}$ substituted aryl, heteroaryl, substituted heteroaryl, alkaryl, and a protecting group, provided that at least one of $R^1$, $R^2$, or $R^3$ is H, $R^5$, $R^7$, $R^8$, $R^9$ and $R^{10}$ independently are selected from the group consisting of H, $C_1$–$C_6$ alkyl, substituted $C_1$–$C_6$ alkyl, $C_6$–$C_{12}$ aryl, and substituted $C_6$–$C_{12}$ aryl, and $R^8$ and $R^9$ together or $R^7$ and $R^9$ together may form a cycloalkyl or substituted cycloalkyl ring, $R^4$ and $R^6$ together form a direct bond or are independently selected from the group consisting of $C_1$–$C_6$ alkyl, substituted $C_1$–$C_6$ alkyl, $C_6$–$C_{12}$ aryl, and substituted $C_6$–$C_{12}$ aryl, and wherein $NR^{10}$ is located at the N-terminus of said peptide, or is located on an amino acid side chain of said peptide.

2. A method according to claim 1, wherein $R^1$ is H.
3. A method according to claim 1, wherein $R^3$ is H.
4. A method according to claim 1, wherein $R^4$ is H.
5. A method according to claim 1, wherein $R^4$ and $R^6$ together form a direct bond.
6. A method according to claim 1, wherein $R^5$ is H.
7. A method according to claim 1, wherein $NR^{10}$ is located at the N-terminus of said peptide.
8. A method according to claim 1, wherein $NR^{10}$ is located on an amino acid side chain of said peptide.
9. A method according to claim 2, wherein $R^2$ is lower alkyl or substituted or unsubstituted phenyl.
10. A method according to claim 9, wherein $R^2$ is H.
11. A method according to claim 10, wherein $R^3$ is H.
12. A method according to claim 11, wherein $R^4$ and $R^6$ together form a direct bond.
13. A method according to claim 11, wherein $R^5$ is H.
14. A method according to claim 13, wherein $R^7$, $R^8$, and $R^9$ each are H.
15. A method according to claim 14, wherein $R^2$ is phenyl.
16. A method according to claim 14, wherein $R^2$ is methyl.
17. A method according to claim 1, wherein $R^8$ and $R^9$ are methyl.
18. A method according to claim 1, wherein said peptide is selected from the group consisting of:

(Chel)γAbuNleDHF$_d$ RWK-NH$_2$, (SEQ ID NO:1)
(Chel)γAbuHSDAVFTDNYTRLRKQMAVKKYLN-SILN-NH$_2$, (SEQ ID NO:2)
KPRRPYTDNYTRLRK(Chel)QMAVKKYLNSILN-NH$_2$, (SEQ ID NO:3)
(Chel)γAbuVFTDNYTRLRKQMAVKKYLNSILN-NH$_2$,
(Chel)γAbuYTRLRKQMAVKKYLNSILN-NH$_2$, (SEQ ID NO:4)
HSDAVFTDNYTRLRK(Chel)QMAVKKYLNSILN-NH$_2$, (SEQ ID NO:5)
(SEQ ID NO:6)<GHWSYK(Chel)LRPG-NH$_2$, <GHYSLK(Chel)WKPG-NH$_2$, (SEQ ID NO:7)
AcNal$_d$ Cpa$_d$ W$_d$ SRK$_d$ (Chel)LRPA$_d$-NH$_2$, (SEQ ID NO:8)
(SEQ ID NO:9) (Chel)AbuSYSNleDHF$_d$ RWK-NH$_2$, Ac-HSDAVFTENYTKLRK(Chel)QNleAAK KYLNDLKKGGT-NH$_2$, (SEQ ID NO:10)
(SEQ ID NO:12) Nal$_d$ Cpa$_d$ W$_d$ SRK$_d$ (Chel)WKPG-NH$_2$, <GHWSYK$_d$ (Chel)LRPG-NH$_2$, (SEQ ID NO:13)
(SEQ ID NO:14) AcK(Chel)F$_d$ CFW$_d$ KTCT-OH, AcK(Chel)DF$_d$ CFW$_d$ KTCT-OH, (SEQ ID NO:15)
(SEQ ID NO:14) AcK(Chel)F$_d$ CFW$_d$ KTCT-ol, AcK(Chel)DF$_d$ CFW$_d$ KTCT-ol, (SEQ ID NO:15)
(SEQ ID NO:16) (Chel)DF$_d$ CFW$_d$ KTCT-OH, K(Chel)DF$_d$ CFW$_d$ KTCT-ol, (SEQ ID NO:15)
(SEQ ID NO:17) K(Chel)KKF$_d$ CFW$_d$ KTCT-ol, K(Chel)KDF$_d$ CFW$_d$ KTCT-OH, (SEQ ID NO:18)
(SEQ ID NO:19) K(Chel)DSF$_d$ CFW$_d$ KTCT-OH, K(Chel)DF$_d$ CFW$_d$ KTCT-OH, (SEQ ID NO:15)
(SEQ ID NO:20) K(Chel)DF$_d$ CFW$_d$ KTCD-NH$_2$, K(Chel)DF$_d$ CFW$_d$ KTCT-NH$_2$, (SEQ ID NO:15)
(SEQ ID NO:18) K(Chel)KDF$_d$ CFW$_d$ KTCT-NHNH$_2$, AcK(Chel)F$_d$ CFW$_d$ KTCT-NHNH$_2$, (SEQ ID NO:14)
(SEQ ID NO:14) K(Chel)F$_d$ CFW$_d$ KTCT-ol, and F$_d$ CFW$_d$ KTCTK(Chel)-NH$_2$, (SEQ ID NO:21) wherein (Chel) is a radiometal-binding moiety.

19. A method according to claim 1, wherein said peptide contains at least one disulfide bond.
20. A method according to claim 19, wherein said peptide is a polypeptide.

* * * * *